United States Patent [19]

Gordon et al.

[11] Patent Number: 4,587,234
[45] Date of Patent: May 6, 1986

[54] CARBOXY AND SUBSTITUTED CARBOXY ALKANOYL AND CYCLOALKANOYL PEPTIDES

[75] Inventors: Eric M. Gordon; Harold N. Weller, III, both of Pennington, N.J.

[73] Assignee: E. R. Squibb & Sons, Inc., Princeton, N.J.

[21] Appl. No.: 663,727

[22] Filed: Oct. 22, 1984

Related U.S. Application Data

[62] Division of Ser. No. 442,681, Nov. 18, 1982, Pat. No. 4,499,079.

[51] Int. Cl.$^4$ .................. A61K 37/43; C07K 5/06
[52] U.S. Cl. ........................ 514/19; 530/800
[58] Field of Search .............. 514/19; 260/112.5 R

[56] References Cited

U.S. PATENT DOCUMENTS

| | | | |
|---|---|---|---|
| 4,052,511 | 10/1977 | Cushman et al. | 424/274 |
| 4,105,789 | 8/1978 | Ondetti et al. | 424/309 |
| 4,248,883 | 2/1981 | Sawayama et al. | 424/274 |
| 4,256,761 | 3/1981 | Suh et al. | 424/282 |
| 4,337,201 | 6/1982 | Petrillo | 548/413 |
| 4,374,829 | 2/1983 | Harris et al. | 424/177 |

FOREIGN PATENT DOCUMENTS

| | | |
|---|---|---|
| 38758 | 10/1981 | European Pat. Off. . |
| 50800 | 5/1982 | European Pat. Off. . |
| 54862 | 6/1982 | European Pat. Off. . |
| 1527 | 3/1981 | South Africa . |
| 2095682 | 10/1982 | United Kingdom . |

*Primary Examiner*—Delbert R. Phillips
*Attorney, Agent, or Firm*—Lawrence S. Levinson; Stephen B. Davis

[57] ABSTRACT

Peptides of the formula

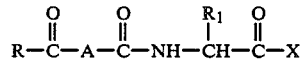

wherein X is various amino or imino acids or esters are useful as hypotensive agents.

9 Claims, No Drawings

CARBOXY AND SUBSTITUTED CARBOXY ALKANOYL AND CYCLOALKANOYL PEPTIDES

This is a division of application Ser. No. 442,681, filed Nov. 18, 1982, now U.S. Pat. No. 4,499,079, issued on Feb. 12, 1985.

BACKGROUND OF THE INVENTION

Various carboxyalkyl peptides possessing angiotensin converting enzyme inhibition activity are disclosed by Patchett et al. in European Patent Application No. 12,401 and by Petrillo et al. in European Patent Application No. 52991.

Various carboxy alkanoyl amino and imino acids possessing angiotensin converting enzyme inhibition activity are disclosed by Cushman et al. in U.S. Pat. No. 4,052,511 and Ondetti et al. in U.S. Pat. No. 4,105,789.

Mercaptoacyl and acylmercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti in U.S. Pat. No. 4,296,113 discloses such compounds wherein the proline has a keto substituent in the 4-position. Krapcho et al. in U.S. Pat. No. 4,310,461 disclose such compounds wherein the proline has an imido, amido, or amino substituent in the 4-position. Petrillo et al. in U.S. Pat. No. 4,296,033 disclose such compounds wherein the proline has an azido substituent in the 4-position. Suh et al. in U.S. Pat. No. 4,256,761 disclose that mercaptoacyl and acylmercaptoacyl derivatives of various N-substituted amino acids also possess angiotensin converting enzyme inhibition activity.

Mercaptoacyl derivatives of dihydroisoindole carboxylic acids and tetrahydroisoquinoline carboxylic acids are disclosed as being useful hypotensive agents by Ondetti et al. in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

Mercaptoacyl and acylmercaptoacyl derivatives of various dipeptides are disclosed as possessing angiotensin converting enzyme inhibition activity by Sawayama et al. in U.S. Pat. No. 4,248,883 and by Ondetti et al. in South African Pat. No. 80/1527.

Petrillo in U.S. Pat. No. 4,337,201 discloses that various esters of phosphinylalkanoyl proline and substituted proline possess angiotensin converting enzyme inhibition activity.

SUMMARY OF THE INVENTION

The novel carboxy and substituted carboxy alkanoyl and cycloalkanoyl peptides of this invention are of the formula (I)

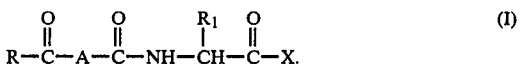

A is

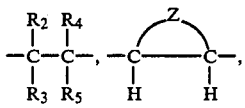

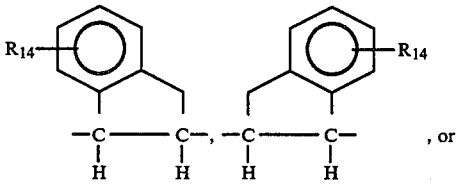

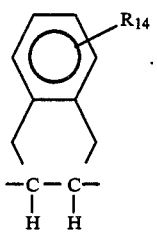

R is hydroxy, lower alkoxy, lower alkyl,

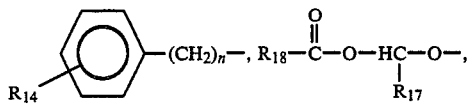

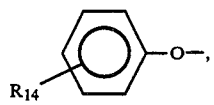

amino, HO—NH—, lower alkoxy —NH—, or —OM wherein M is an alkali metal salt ion such as sodium, potassium, or lithium or an alkaline earth metal salt ion such as calcium or magnesium.

$R_1$ is hydrogen, lower alkyl, halo substituted lower alkyl,

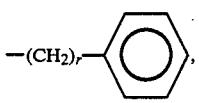

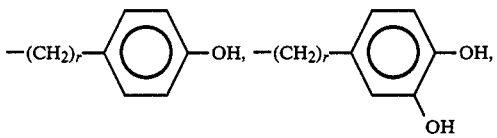

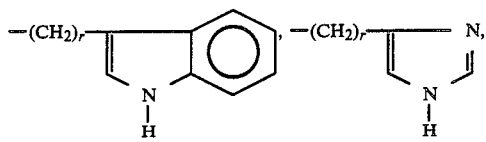, 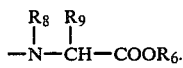

—(CH$_2$)$_r$—NH$_2$, —(CH$_2$)$_r$—SH, —(CH$_2$)$_r$—OH,

—(CH$_2$)$_r$—S—lower alkyl, 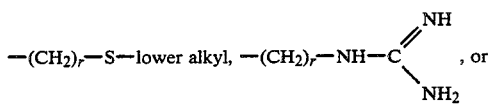, or

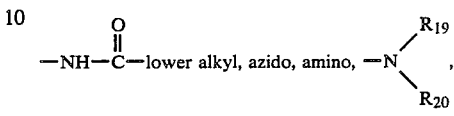

R$_7$ is hydrogen, lower alkyl, halogen, keto, hydroxy,

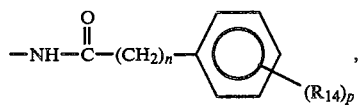

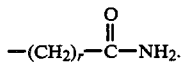

R$_2$, R$_3$, R$_4$, and R$_5$ are independently selected from hydrogen, lower alkyl, lower alkoxy, lower alkylthio, cycloalkyl,

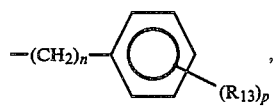

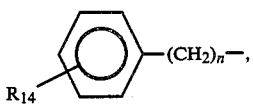

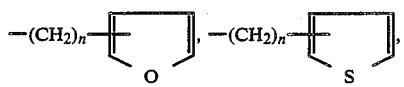

hydroxy, amino, halo, halo substituted lower alkyl, hydroxy substituted lower alkyl, amino substituted lower alkyl,

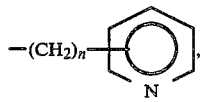

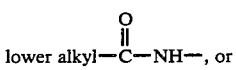

a 1- or 2-naphthyl of the formula

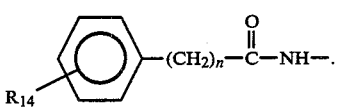

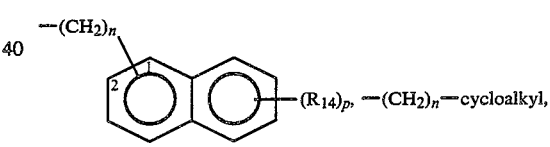

X is an amino or imino acid of the formula

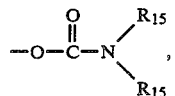

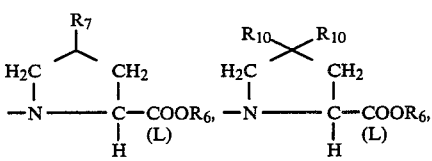

—O—lower alkyl,

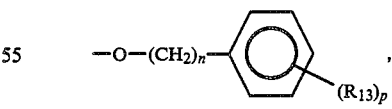

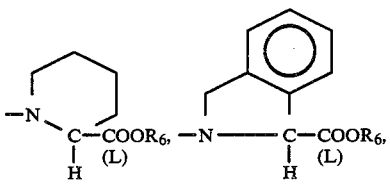

a 1- or 2-naphthyloxy of the formula

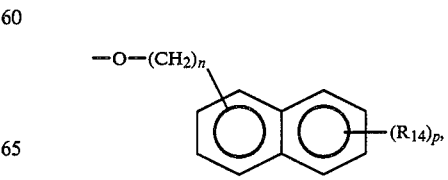

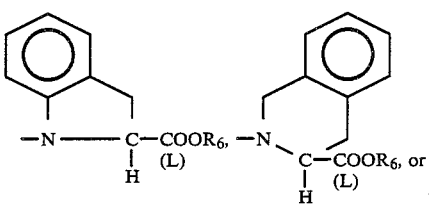

—S—lower alkyl,

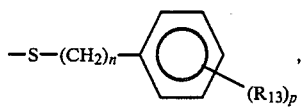

or a 1- or 2-naphthylthio of the formula

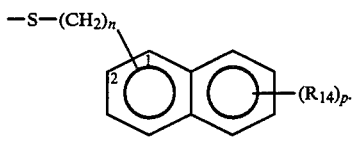

$R_{10}$ is halogen or $-Y-R_{16}$.

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

n is zero, one, two, three, or four.

p is one, two or three provided that p is more than one only if $R_{13}$ or $R_{14}$ is hdyrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

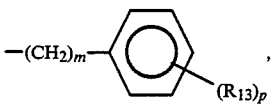

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_8$ is hydrogen, lower alkyl, cycloalkyl of 3 to 7 carbons, or

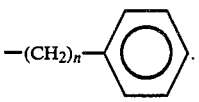

$R_9$ is hydrogen, lower alkyl,

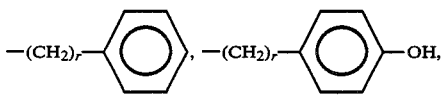

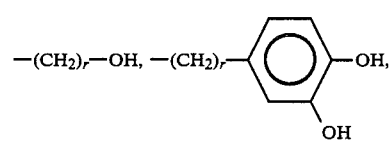

-continued

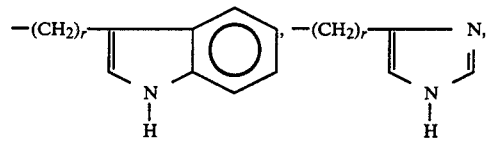

$-(CH_2)_r-NH_2$, $-(CH_2)_r-SH$, $-(CH_2)_r-S-$lower alkyl,

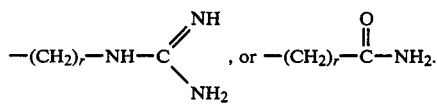

r is an integer from 1 to 4.

$R_{19}$ is lower alkyl, benzyl, or phenethyl.

$R_{20}$ is hydrogen, lower alkyl, benzyl or phenethyl.

$R_6$ is hydrogen, lower alkyl, benzyl, benzhydryl, a salt forming ion such as an alkali metal salt ion such as sodium, potassium, or lithium or an alkaline earth metal salt ion such as calcium or magnesium, or

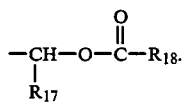

$R_{17}$ is hydrogen, lower alkyl, cycloalkyl of 3 to 7 carbons, or phenyl.

$R_{18}$ is hydrogen, lower alkyl, lower alkoxy, or phenyl.

Z completes a cycloalkyl ring of 3 to 10 carbons; said cycloalkyl ring in which one of the carbon atoms is substituted by a lower alkyl of 1 to 4 carbons, lower alkoxy of 1 to 4 carbons, lower alkylthio of 1 to 4 carbons, halo, trifluoromethyl, or hydroxy group; a cycloalkenyl ring of 5 to 7 carbons; or a cycloalkadienyl ring of 6 or 7 carbons.

DETAILED DESCRIPTION OF THE INVENTION

This invention in its broadest aspects relates to the carboxy and substituted carboxy alkanoyl and cycloalkanoyl peptide compounds of formula I above, to compositions containing such compounds, and to the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the terms hydroxy substituted lower alkyl and amino substituted lower alkyl refer to such lower alkyl groups in which one or more hydrogens have been replaced by hydroxy and amino groups such as hydroxymethyl, 2-hydroxyethyl, 3-aminopropyl, etc.

The symbols

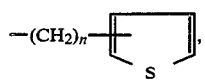

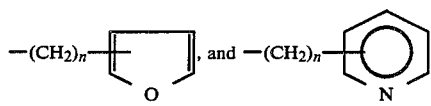

represent that the alkylene bridge is attached to an available carbon atom.

The compounds of formula I may be obtained by coupling a carboxylic acid of the formula

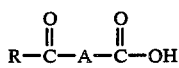 (II)

with the peptide ester of the formula

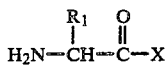 (III)

wherein $R_6$ in the definition of X is an easily removable ester protecting group such as benzhydryl, benzyl or t-butyl. This coupling reaction can be accomplished using any one of the numerous techniques well known in the art. For example, the reaction can be performed in the presence of a coupling agent such as a carbodiimide, preferably dicyclohexylcarbodiimide. Alternatively, the carboxylic acid of formula II can be activated by formation of its mixed anhydride, symmetrical anhydride, acid chloride or active ester or by use of Woodward reagent K or N-ethoxycarbonyl-2-ethoxy 1,2-dihydroquinoline. Following completion of the coupling, the $R_6$ protecting group is removed for example by hydrogenation when $R_6$ is benzyl or treatment with trifluoroacetic acid when $R_6$ is t-butyl to yield the products of formula I wherein $R_6$ is hydrogen.

In the above reaction if any or all of R, $R_1$, $R_2$, $R_3$, $R_4$, $R_5$, $R_8$, or $R_9$ are hydroxy, amino,

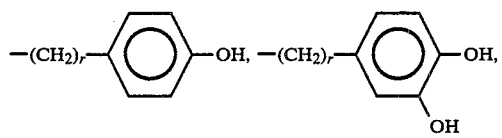

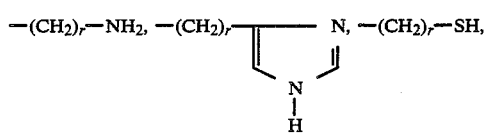

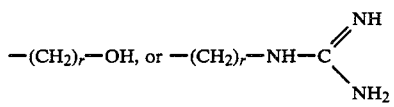

then the hydroxyl, amino, imidazolyl, mercaptan or guanidinyl function should be protected during the reaction. Suitable protecting groups include benzyloxycarbonyl, t-butoxycarbonyl, t-butyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benzhydryl can be chemically treated such as with sodium hydroxide in aqueous dioxane to yield the products of formula I wherein $R_6$ is hydrogen. The benzyl and benzhydryl esters can also be hydrogenated, for example, by treating with hydrogen in the presence of a palladium on carbon catalyst.

The ester products of formula I wherein $R_6$ is

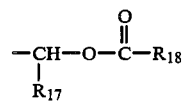

may be obtained by employing the peptide of formula III in the above reactions with such ester group already in place. Such ester reactants can be prepared by treating the peptide of formula III wherein $R_6$ is hydrogen with a reagent such as

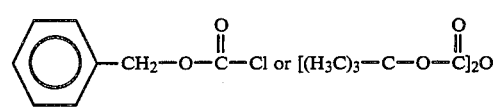

so as to protect the N-atom. The protected peptide is then reacted in the presence of a base with a compound of the formula

 (IV)

wherein L is a leaving group such as chlorine, bromine, tolylsulfonyloxy, etc., followed by removal of the N-protecting group such as by treatment with acid or hydrogenation.

The ester products of formula I wherein $R_6$ is

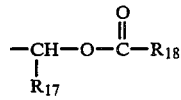

can also be obtained by treating the product of formula I wherein $R_6$ is hydrogen with a molar excess of the compound of formula IV. The diester products wherein

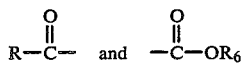

are the same and are

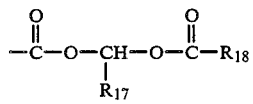

can be obtained by treating the product of formula I wherein

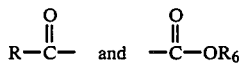

are both

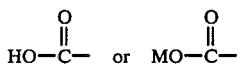

with two or more equivalents of the compound of formula IV.

The ester products of formula I wherein R is

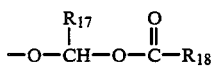

can be obtained by employing the carboxylic acid of formula II in the coupling reaction with the R ester group already in place. Alternatively, these ester products can be obtained by treating the product of formula I wherein R is hydroxy or —OM and $R_6$ is benzyl or benzhydryl with the compound of formula IV in the presence of base. Removal of the $R_6$ ester group such as by hydrogenation yields the products of formula I wherein R is

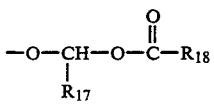

and $R_6$ is hydrogen.

The peptide ester of formula III may be obtained by coupling the hydrochloride salt of the amino or imino acid ester of the formula

HX    (V)

wherein $R_6$ is, for example, benzyl with the N-protected amino acid of the formula

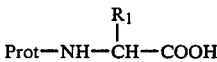

wherein Prot is a protecting group such as

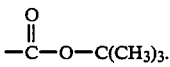

Preferably, this reaction is performed in the presence of a coupling agent such as dicyclohexylcarbodiimide. Removal of the N-protecting group, for example, by treatment with trifluoroacetic acid yields the peptide ester of formula III.

The carboxylic acids of formula II are prepared by conventional procedures. Many of these compounds are described by Cushman et al. in U.S. Pat. No. 4,052,511 noted above.

Preferred compounds of this invention with respect to the peptide part of the structure of formula I are those wherein:
X is

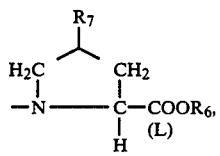

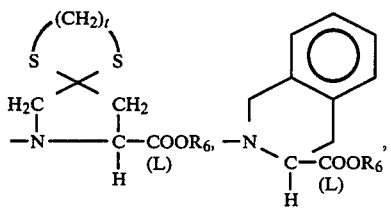

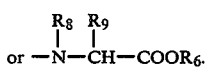

$R_1$ and $R_9$ are independently selected from hydrogen, straight or branched chain lower alkyl of 1 to 4 carbons, —$CH_2OH$,

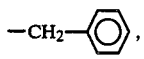

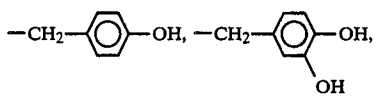

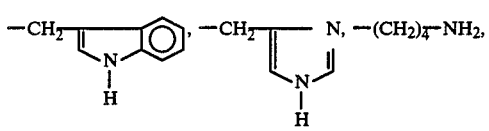

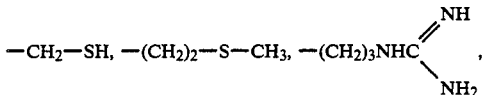

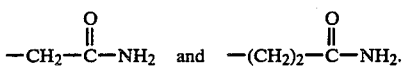

$R_7$ is hydrogen, cyclohexyl, lower alkoxy of 1 to 4 carbons,

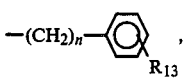

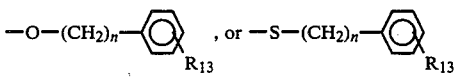

wherein n is zero, one, or two and $R_{13}$ is hydrogen, methyl, methoxy, methylthio, Cl, Br, F, or hydroxy.

t is two or three.

$R_6$ is hydrogen, an alkali metal salt, straight or branched chain alkyl of 1 to 4 carbons, or

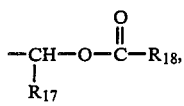

$R_{17}$ is hydrogen, straight or branched chain lower alkyl of 1 to 4 carbons, or cyclohexyl and $R_{18}$ is straight or branched chain lower alkyl of 1 to 4 carbons or phenyl.

$R_8$ is hydrogen or cycloalkyl of 5 to 7 carbons.

Most preferred compounds of this invention with respect to the peptide part of the structure of formula I are those having the peptide

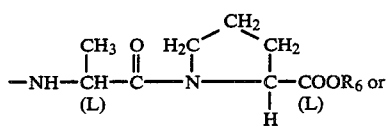

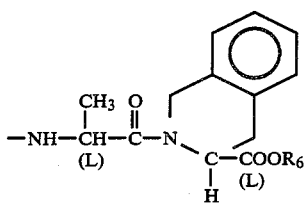

wherein $R_6$ is hydrogen, ethyl,

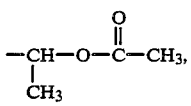

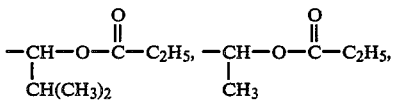

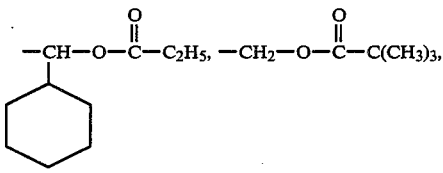

or an alkali metal salt.

Preferred compounds of this invention with respect to the carboxyalkanoyl and carboxycycloalkanoyl portion of the structure of formula I are those wherein:

A is

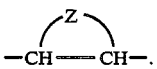

Z completes a cycloalkyl ring of 4 to 7 carbons, a cycloalkyl ring of 4 to 7 carbons wherein one of the carbons is substituted by a methyl, methoxy, methylthio, Cl, Br, F, or hydroxy, or a cyclohexenyl ring.

R is hydroxy, ethoxy, —OM, or

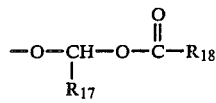

wherein $R_{17}$ is hydrogen, straight or branched chain lower alkyl of 1 to 4 carbons, or cyclohexyl and $R_{18}$ is straight or branched chain lower alkyl of 1 to 4 carbons or phenyl, especially wherein R is hydroxy or —OM.

The compounds of formula I wherein $R_6$ is hydrogen and/or R is hydroxy form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The peptide portion of the molecule of the products of formula I represented by

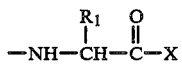

is in the L-configuration. Depending upon the definition of $R_2$, $R_3$, $R_4$ and $R_5$ one or two asymmetric centers may be present in the carboxy alkanoyl sidechain. When A is

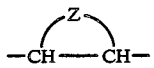

the carboxy cycloalkanoyl sidechain gives rise to cis-trans isomerism in addition to the asymmetric center. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted also give rise to cis-trans isomerism. The configuration of the final product will depend upon the configuration of the $R_7$ substituent in the starting material of formula V.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE) to angiotensin II. The latter is and active pressor substance which has been implicated as the causative agent in several forms of hypertension in various mammalian species, e.g., humans. The compounds of this invention intervene in the angiotensinogen → (renin) → angiotensin I → angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

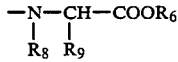

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[N-(3-Carboxy-1-oxopropyl)-L-alanyl]-L-proline, dilithium salt (a) 1-[N-(3-Carboxy-1-oxopropyl)-L-alanyl]-L-proline, phenylmethyl ester Diisopropylethylamine (0.85 ml., 4.9 mmole) is added to a mixture of succinic anhydride (0.49 g., 4.9 mmole) and L-alanyl-L-proline, phenylmethyl ester, tosylate salt (2.2 g., 4.9 mmole) in tetrahydrofuran (50 ml.). The resulting mixture is stirred at 25° for 17 hours, after which it is concentrated. The residue is redissolved in ethyl acetate and is washed with water and extracted with 10% aqueous sodium bicarbonate solution. The aqueous extract is acidified with hydrochloric acid and then extracted with ethyl acetate. The ethyl acetate phase is dried and concentrated to give 1-[N-(3-carboxy-1-oxopropyl)-L-alanyl]-L-proline, phenylmethyl ester as a clear oil.

(b) 1-[N-(3-Carboxy-1-oxopropyl)-L-alanyl]-L-proline, dilithium salt

A solution of the phenylmethyl ester product from part (a) (700 mg., 1.86 mmole) in 95% ethanol (100 ml.) containing 10% palladium on carbon catalyst (100 mg.) is hydrogenated at 25 psi in a Parr apparatus for 19 hours, after which it is filtered and concentrated to give 1-[N-(3-carboxy-1-oxopropyl)-L-alanyl]-L-proline as a colorless oil. This diacid product is dissolved in water, passed through a column of AG 50 W X8 (Li+) and lyophilized to give 1-[N-(3-carboxy-1-oxopropyl)-L-alanyl]-L-proline, dilithium salt as a stable, off white solid which is homogeneous by TLC ($R_f$ 0.6, silica gel, 3:1:1 n-butanol:acetic acid: water). $[\alpha]_D = -100°$ (1.5% water).

Anal. Calc'd for $C_{12}H_{16}N_2O_6Li_2 \cdot 2.2H_2O$:
C, 42.69, H, 6.09; N, 8.30; Li, 4.11.
Found: C, 42.69, H, 5.95; N, 8.06; Li, 4.03.

EXAMPLE 2

1-[N-(1,4-Dioxo-4-phenylbutyl)-L-alanyl]-L-proline (a) 1-[N-(1,4-Dioxo-4-phenylbutyl)-L-alanyl]-L-proline, phenylmethyl ester To a suspension of L-alanyl-L-proline, phenylmethyl ester, tosylate salt (5.0 g., 11.2 mmole) in tetrahydrofuran (100 ml.) are added diisopropylethylamine (2.0 ml., 11.2 mmole), 3-benzoyl propionic acid (2.0 g., 11.2 mmole), 1-hydroxybenzotriazole hydrate (1.5 g., 11.2 mmole), and dicyclohexylcarbodiimide (2.3 g., 11.2 mmole). The resulting mixture is stirred at 25° for 24 hours, after which it is filtered and concentrated by rotary evaporation. The residue is dissolved in ethyl acetate and the solution is washed sequentially with 1N hydrochloric acid and 10% aqueous sodium bicarbonate. The solution is concentrated and the residue is passed through a short column of activated magnesium silicate available under the trademark Florisil (chloroform to ethyl acetate solvent gradient). Fractions are collected and those containing the major product ($R_f$ 0.4 silica gel, ethyl acetate) are concentrated to give 2.5 g. of 1-[N-(1,4-dioxo-4-phenylbutyl)-L-alanyl]-L-proline, phenylmethyl ester as a bright orange oil.

(b) 1-[N-(1,4-Dioxo-4-phenylbutyl)-L-alanyl]-L-proline

A mixture of the phenylmethyl ester product from part (a) (1.3 g., 3.0 mmole), methanol (3.5 ml.), ethanol (3.5 ml.), water (3.5 ml.), and 1N aqueous sodium hydroxide solution (3.5 ml., 3.5 mmole) is stirred at 25° for 17 hours, after which it is partially concentrated by rotary evaporation (to remove volatile alcohols). The solution is then diluted with water and washed with ethyl acetate (the ethyl acetate layer is discarded). The aqueous layer is acidified with hydrochloric acid and extracted twice with ethyl acetate. The extracts are combined, dried, and concentrated to give 1.0 g. of the desired product as a pale yellow oil. This oil is dissolved in water (150 ml.), filtered through charcoal, and lyophilized to give 500 mg. of 1-[N-(1,4-dioxo-4-phenylbutyl)-L-alanyl]-L-proline as a fluffy white powder. TLC ($R_f$ 0.4 on silica gel, 1:1 methanol:ethyl acetate). $[\alpha]_D = -80°$ (1% chloroform).

Anal. Calc'd. for $C_{18}H_{22}N_2O_5 \cdot 1.2H_2O$:
C, 58.74; H, 6.68; N, 7.61.
Found: C, 58.79; H, 6.49; N, 7.73.

EXAMPLE 3

1-[N-(4-Ethoxy-1,4-dioxobutyl-L-alanyl]-L-proline, 1,1-dimethylethanamine salt (1:1)

(a) Succinic acid, monoethyl ester

To a mixture of succinic anhydride (30 g., 0.30 mole) in ethanol (200 ml.) is added diisopropylethylamine (2 ml.). The resulting solution is stirred at ambient temperature for 5 hours, after which it is concentrated by rotary evaporation. The residue is dissolved in ethyl acetate and the solution is washed sequentially with 1N hydrochloric acid and water, dried, and concentrated to give a colorless oil which on cold storage solidifies to 32 g. of succinic acid, monoethyl ester.

(b) 1-[N-(4-Ethoxy-1,4-dioxobutyl)-L-alanyl]-L-proline, phenylmethyl ester

To a mixture of succinic acid, monoethyl ester (3.3 g., 22 mmole) and L-alanyl-L-proline, phenylmethyl ester, tosylate salt (10 g., 22 mmole) in tetrahydrofuran (200 ml.) are added diisopropylethylamine (4 ml., 22 mmole), dicyclohexylcarbodiimide (4.6 g., 22 mmole) and 1-hydroxybenzotriazole hydrate (3 g., 22 mmole). The resulting mixture is stirred at 25° for 19 hours, after which it is filtered and concentrated. The residue is dissolved in ethyl acetate and the solution is washed sequentially with 1N hydrochloric acid and 10% aqueous sodium bicarbonate solution, dried, and concentrated. The residue is dissolved in ether, millipore filtered, and reconcentrated to give 7.9 g. of 1-[N-(4-ethoxy-1,4-dioxobutyl)-L-alanyl]-L-proline, phenylmethyl ester.

(c) 1-[N-(4-Ethoxy-1,4-dioxobutyl)-L-alanyl]-L-proline, 1,1-dimethylethanamine salt (1:1)

A mixture of the phenylmethyl ester product from part (b) (2.3 g., 5.7 mmole), 10% palladium on carbon catalyst (200 mg.) and ethanol (150 ml.) is hydrogenated on a Parr apparatus at 40 psi for 15 hours, after which it is filtered and concentrated. The residue is chromatographed (Silic AR CC-4), eluting with ethyl acetate " methanol gradient. Fractions containing the major product($R_f$ 0.3 silica gel, methanol:ethyl acetate 1:1) are combined and concentrated to give 1.5 g. of 1-[N-(4-ethoxy-1,4-dioxobutyl)-L-alanyl]-L-proline. To a solution of this acid product (800 mg., 2.55 mmole) in acetonitrile (10 ml.) is added tert-butylamine (300 μl.). The white precipitate which forms is collected, washed with ether, and dried to give 800 mg. of 1-[N-(4-ethoxy-1,4-dioxobutyl)-L-alanyl]-L-proline, 1,1-dimethylethanamine salt (1:1); m.p. 125°–128°. TLC ($R_f$ 0.22, 0.07 silica gel, 7:1 benzene:acetic acid). $[\alpha]_D = -98°$ (c 1.5 water).

Anal. Calc'd. for $C_{18}H_{33}N_3O_6 \cdot 0.34H_{20}$:
C, 54.92; H, 8.63; N, 10.67.
Found: C, 54.92; H, 8.34; N, 10.59.

EXAMPLE 4

1-[N-[4-(Hydroxyamino)-1,4-dioxobutyl]-L-alanyl]-L-proline (a) 4-Oxo-4-[(phenylmethoxy)amino]butanoic acid A mixture of succinic anhydride (15 g., 0.15 mole), O-benzyl hydroxylamine hydrochloride (24 g., 0.15 mole), and diisopropylethylamine (26 ml. 0.15 mole) in tetrahydrofuran is stirred at 25° for 19 hours, after which it is concentrated by rotary evaporation. The residue is dissolved in aqueous 1N sodium hydroxide and washed with ethyl acetate. The aqueous layer is acidified with 1N hydrochloric acid and extracted three times with methylene chloride. The combined extract is dried and concentrated. The residue is triturated with ether to give 13.5 g. of 4-oxo-4-[(phenylmethoxy) amino]butanoic acid as a white powder.

(b) 1-[N-[N-[(Phenylmethoxy)amino]-1,4-dioxobutyl]-L-alanyl]-L-proline, phenylmethyl ester A mixture of 4-oxo-4-[(phenylmethoxy)amino]butanoic acid (2.5 g., 11.2 mmole), L-alanyl-L-proline, phenylmethyl ester, tosylate salt (5.0 g., 11.2 mmole), diisopropylethylamine (2 ml., 11.2 mmole), 1-hydroxybenzotriazole (1.5 g., 11.2 mmole), and dicyclohexylcarbodiimide (2.3 g., 11.2 mmole) in tetrahydrofuran (100 ml.) is stirred at 25° for 19 hours, after which it is concentrated by rotary evaporation. The residue is dissolved in ethyl acetate and filtered. The filtrate is washed sequentially with 1N hydrochloric acid and 10% aqueous sodium bicarbonate solution, dried, and concentrated. The residue is triturated with cold ether to give 2 g. of semi-solid material which is then chromatographed on Florisil, eluting first with ethyl acetate then with ethyl acetate/methanol to give 750 mg. of 1-[N-[4-[(phenylmethoxy)amino]-1,4-dioxobutyl]-L-alanyl]-L-proline, phenylmethyl ester as a foamy semi-solid.

(c) 1-[N-[4-(Hydroxyamino)-1,4-dioxobutyl]-L-alanyl]-L-proline

A mixture of the phenylmethyl ester product from part (b) (750 mg., 1.5 mmole), 10% palladium on carbon catalyst (150 mg.), ethyl acetate (100 ml.), and ethanol (100 ml.) is hydrogenated on a Parr apparatus at 30 psi for two hours, after which it is filtered and concentrated. The pinkish residue is chromatographed on HP-20 (high porous polystyrene resin, available under the trademark MCI gel) (water to ethanol elution gradient). Fractions are monitored with ferric chloride stain; those giving a positive stain are concentrated and recrystallized from water to give 100 mg. of 1-[N-[4-(hydroxyamino)-1,4-dioxobutyl]-L-alanyl]-L-proline as off-white needles; m.p. 195°–196°. TLC ($R_f$ 0.57 silica gel; 1:1:1:1 ethyl acetate:acetic acid:n-butanol:water). $[\alpha]_D^{20} = -131°$ (c =1, water).

Anal. Cal'd for $C_{12}H_{19}N_3O_6 \cdot 0.75 H_2O$:

C, 45.79; H, 6.56; N, 13.35.
Found: C, 45.66; H, 6.24; N, 13.14.

EXAMPLE 5

(±)-1-[N-[2-(Carboxymethyl)-1-oxo-3-phenylpropyl]-L-alanyl]-L-proline, dilithium salt (a) 2-(Phenylmethylene)butanedioic acid, 4-mono-(phenylmethyl)ester Benzylidene succinic acid (12.2 g., 59 mmole) [prepared as described in JACS, Vol. 90, p. 3495 (1968)]is refluxed in acetic anhydride (100 ml.) for one hour. The excess acetic anhydride is removed by distillation and the residue is concentrated to dryness.

The residue is then refluxed in benzyl alcohol (65 ml.) for 3 hours. Excess benzyl alcohol is removed by distillation. The remaining material is stirred in 10% sodium bicarbonate solution and filtered. The filtrate is acidified with concentrated hydrochloric acid and extracted with ether. The combined ether layers are dried (MgSO$_4$) and concentrated leaving 1.1 g. (3.7 mmole) of pale yellow crystals. The insoluble sludge which had been removed by filtration is dissolved in ether and extracted with 10% sodium bicarbonate solution. The aqueous layer is then treated as described above. Both residues are combined and applied to a Florisil column and eluted with benzene:acetic acid (7:1) solution. Fractions containing the major product (R$_f$ 0.6 silica gel, benzene:acetic acid, 7:1) are combined and concentrated to give 1.9 g. 2-(phenylmethylene) butanedioic acid, 4-mono(phenylmethyl) ester.

(b) 1-[N-[1,4-Dioxo-4-(phenylmethoxy)-2-(phenylmethylene)butyl]-L-alanyl]-L-proline, phenylmethyl ester To a slurry of L-alanyl-L-proline, phenylmethyl ester, tosylate salt (2.7 g., 6.0 mmole) in dry tetrahydrofuran (100 ml.) are added 2-(phenylmethylene) butanedioic acid, 4-mono(phenylmethyl)ester (1.8 g., 6.0 mmole),1-hydroxybenzotriazole hydrate (0.8 g., 6.0 mmole), and dicyclohexylcarbodiimide (1.3 g., 6.0 mmole). To this mixture is added diisopropylethylamine (1.1 ml., 6.0 mmole) at which time the solution clears then clouds immediately. The mixture is stirred at room temperature for 24 hours. The resulting solution is then filtered, concentrated, dissolved in ethyl acetate and filtered again. The filtrate is washed with 1N hydrochloric acid and 10% sodium bicarbonate solution, dried (MgSO$_4$) and concentrated to give 2.9 g. of yellow oil. This product is chromatographed on LP-1 (silica gel) using ethyl acetate:hexane (1:1) as eluant. The fractions containing the major product (R$_f$ 0.6 silica gel, ethyl acetate) are combined and concentrated to give 0.95 g. (1.7 mmole) of 1-[N-[1,4-dioxo-4-(phenylmethoxy)-2-(phenylmethylene)butyl]-L-alanyl]-L-proline, phenylmethyl ester as a pale yellow oil.

(c) (±)-1-[N-[2-(Carboxymethyl)-1-oxo-3-phenyl-propyl]-L-alanyl]-L-proline, dilithium salt The phenylmethyl ester product from part (b) (950 mg., 1.7 mmole) is added to a stirring suspension of 10% palladium on carbon catalyst (90 mg.) in ethanol (200 ml.). The solution is purged with argon, then hydrogenated on a Parr apparatus at 30 psi for 4 days (an additional 90 mg. of catalyst is added after 22 hours). The mixture is again purged with argon, filtered (Celite), and millipore filtered. The filtrate is concentrated and redissolved in 1.5 mole equivalent of 1N lithium hydroxide. This solution is passed through an AG50WX2 (Li+) column eluting with water. The resulting material is applied to a column of HP-20 and eluted with water. Fractions containing the major product are combined and concentrated. The foamy product is dissolved in water and lyophilized to give 340 mg. (0.87 mmole) of (±)-1-[N-[2-(carboxymethyl)-1-oxo-3-phenylpropyl]-L-alanyl]-L-proline, dilithium salt as a white solid. TLC (R$_f$ 0.77 silica gel, n-butanol:acetic acid:water:ethyl acetate, 1:1:1:1). $[\alpha]_D^{25} = -98°$ (c =1.2, water).

Anal. Calc'd. for C$_{19}$H$_{22}$N$_2$O$_6$Li$_2$ . 2.85 H$_2$O:
C, 51.92; H, 6.35; N, 6.37; Li, 3.16.
Found: C, 51.92; H, 6.32; N, 6.31; Li, 3.17.

EXAMPLE 6

(±)-1-[N-(3-Carboxy-1-oxo-4-phenylbutyl)-L-alanyl]-L-proline, dilithium salt (a) Dibenzyl succinate To a solution of succinic anhydride (10 g., 0.10 mole) and benzyl alcohol (22 g., 0.2 mole) in methylene chloride (250 ml.) are added dicyclohexylcarbodiimide (21 g., 0.1 mole) and dimethylaminopyridine (1.0 g.). The mixture is stirred at 25° for 20 hours, after which it is filtered. The filtrate is washed sequentially with 5% potassium bisulfate solution and 10% sodium bicarbonate solution, dried, and concentrated. The residue is dissolved in ether, filtered, and reconcentrated to give 25 g. of dibenzyl succinate.

(b) 2-(Phenylmethylene)butanedioic acid, 1-mono-(phenylmethyl)ester

A mixture of dibenzyl succinate (22 g., 0.074 mole), benzaldehyde (7.9 g., 0.074 mole) and potassium t-butoxide (8.3 g., 0.074 mole) in tert-butanol (100 ml.) is heated at reflux for 3.5 hours. After cooling to room temperature, the mixture is acidified with 1hydrochoric acid and concentrated by rotary evaporation. Ether and water are then added and the mixture is extracted twice with ether. The ether layers are combined and extracted twice with 10% sodium bicarbonate solution. The combined bicarbonate layers are acidified with hydrochloric acid and extracted twice with ether. The extract is dried and concentrated to give 8.0 g. of a viscous brown oil. Filtration through a short column of Florisil (eluting with 7:1 benzene:acetic acid) gives 5.5 g. of 2-(phenylmethylene)butanedioic acid, 1-mono-(phenylmethyl)ester as a pale yellow oil.

(c) 1-[N-[1,4-Dioxo-4-(phenylmethoxy)-3-(phenylmethylene)butyl]-L-alanyl]-L-proline, phenylmethyl ester To a mixture of 2-(phenylmethylene)butanedioic acid, 1-mono(phenylmethyl) ester (5.5 g., 18.6 mmole) and L-alanyl-L-proline, phenylmethyl ester, tosylate salt (8.3 g., 18.6 mmole in tetrahydrofuran (200 ml.) are added diisopropylethylamine (3.23 ml., 18.6 mmole), dicyclohexylcarbodiimide (3.8 g., 18.6 mmole) and 1-hydroxybenzotriazole hydrate (2.5 g., 18.6 mmole). The resulting mixture is stirred at 25° for 24 hours, after which it is concentrated by rotary evaporation. Ethyl acetate is added to the residue and the resulting solution is filtered, washed sequentially with 1N hydrochloric acid and 10% aqueous sodium bicarbonate, dried and concentrated. The residue is dissolved in ether, filtered, and reconcentrated to give a dark green oil (9 g.). Flash chromatography of this material (LP-1, 1:1 hexane:ethyl acetate) gives 4.0 g. of 1-[N-[1,4-dioxo-4-(phenylmethoxy)-3-(phenylmethylene)butyl]-L-alanyl]-L-proline, phenylmethyl ester as the major product.

(d)
(±)-1-[N-(3-Carboxy-1-oxo-4-phenylbutyl)-L-alanyl]-L-proline, dilithium salt A mixture of the phenylmethyl ester product from part (c) (1.5 g., 2.7 mmole), 10% palladium on carbon catalyst (200 mg.), ethanol (150 ml.) and water (50 ml.) is hydrogenated on a Parr apparatus at 50 psi for 24 hours, after which hydrogenation is stopped and fresh catalyst is added (200 mg.). Hydrogenation is then continued (50 psi) for 3 days, after which the mixture is filtered and concentrated. The residue is dissolved in 2.7 ml. of 1.0N lithium hydroxide and is passed through a column of excess AG50WX2 (Li+), eluting with water. The eluant is concentrated and the residue is chromatographed on HP-20 (eluting with water). Fractions containing the major product are combined and lyophilized to give (±)-1-[N-(3-carboxy-1-oxo-4-phenylbutyl)-L-alanyl]-L-proline, dilithium salt as a white powder. TLC ($R_f$ 0.45 silica gel, ethyl acetate:pyridine:acetic acid:water, 45:20:6:11). $[\alpha]_D = -60°$ (c =1.5%, water).
Anal. Calc'd. for $C_{19}H_{22}N_2O_6Li_2 \cdot 3.3\ H_2O$:
C, 50.98; H, 6.44; N, 6.26; Li, 3.10.
Found: C, 50.98; H, 6.27; N, 5.96; Li, 3.00.

EXAMPLE 7
1-[N-[2-(Carboxymethyl)-1-oxo-4-phenylbutyl]-L-alanyl]-L-proline (iosmer A) and (isomer B)

(a) 2-(Methoxycarbonyl)butanedioic acid, 4-mono(1,1-dimethylethyl)ester, 1-monomethyl ester To a suspension of sodium hydride (100 mmole, hexane washed) in tetrahydrofuran (200 ml.) under argon is added dimethylmalonate (12.2 g., 92 mmole) over 30 minutes. When gas evolution subsides, the mixture is heated at reflux for 30 minutes. While still at reflux, tert-butyl bromoacetate (15 ml., 92 mmole) is added. The resulting mixture is heated at reflux for 3 hours, after which it is poured into water and concentrated by rotary evaporation. The residue is partitioned between ether and water, and extracted 3 times with ether. The combined extract is washed with water, dried, and concentrated. The residue is distilled to give 16 g. of 2-(methoxycarbonyl) butanedioic acid, 4-mono(1,1-dimethylethyl) ester, 1-monomethyl ester; b.p. 105°–115°/1 torr.

(b) 2-(Methoxycarbonyl)-2-(2-phenylethyl)butane-dioic acid, 4-mono(1,1-dimethylethyl)ester, 1-monomethyl ester To a suspension of sodium hydride (37.5 mmole, pentane washed) in tetrahydrofuran (100 ml.) is added 2-(methoxycarbonyl)butanedioic acid, 4-mono (1,1-dimethylethyl)ester, 1-monomethyl ester (8.0 g., 32.5 mmole). The resulting mixture is heated slowly to reflux (gas evolution). Heating at reflux is continued for 30 minutes, after which phenethyl bromide (8.9 g., 48.1 mmole) is added. The mixture is heated at reflux for 20 hours, after which it is poured into water and extracted three times with ether. The combined extract is washed sequentially with aqueous sodium bisulfate and 10% sodium bicarbonate, dried, and concentrated. A few crystals of anhydrous sodium carbonate are added to the residue and the volatiles are removed by Kugelrohr distillation (175°/2 torr). The residue is dissolved in hexane:ethyl acetate (4:1) and filtered through a pad of silica gel. Concentration gives 6.75 g. of 2-(methoxycarbonyl)-2-(2-phenylethyl)butanedioic acid, 4-mono(1,1-dimethylethyl)ester, 1-monomethyl ester.

(c) 2-(2-(Phenylethyl)butanedioic acid, 4-mono(1,1-dimethylethyl) ester

To a stirred suspension of sodium cyanide (6.57 g.) in hexamethylphosphoramide (250 ml.) at 75° is added 2-(methoxycarbonyl)-2-(2-phenylethyl) butanedioic acid, 4-mono(1,1-dimethylethyl)ester, 1-monomethyl ester (6.75 g., 18.6 mmole). The resulting mixture is stirred at 75° for 5 hours, after which it is poured into 1N hydrochloric acid (1 l.). The mixture is extracted three times with ether and the combined ether extract is then extracted with 10% sodium bicarbonate solution. Concentration of the ether extract gives 2 g. of 2-(2-phenylethyl)butanedioic acid, -4-mono (1,1-dimethylethyl)ester, 1-monomethyl ester.

The bicarbonate extract is acidified with hydrochloric acid and extracted with ether. The extract is dried and concentrated to give a red oil. This oil is taken up in ether (10 ml.) and dicyclohexylamine (1.0 ml.) and hexane (10 ml.) are added. A heavy black oil separates in the bottom of the flask, leaving a homogeneous solution above. The solution is decanted from the oil, filtered through charcoal, and cooled. The solid which forms is recrystallized from ether to give 2-(2-phenylethyl)-butanedioic acid, 4-mono(1,1-dimethylethyl)ester, dicyclohexylamine salt; m.p. 120°–125°. This salt is partitioned between 1N hydrochloric acid and ethyl acetate. The ethyl acetate layer is dried and concentrated to give 200 mg. of 2-(2-phenylethyl)butanedioic acid, 4-mono(1,1-dimethylethyl)ester as a pale yellow oil.

A mixture of 2-(2-phenylethyl)butanedioic acid, 4-mono(1,1-dimethylethyl)ester, 1-monomethyl ester (2 g., 6.8 mmole) in aqueous 1N sodium hydroxide (7 ml., 7 mmole) is stirred at 25° for 3 days, after which is is diluted with water and washed with ether. The extract is dried and concentrated. A dicyclohexylamine salt is prepared from the residue as described above. This salt is partitioned between 1N hydrochloric acid and ethyl acetate. The ethyl acetate layer is filtered through silica gel and concentrated to give an additional 400 mg. of 2-(2-phenylethyl)butanedioic acid, 4-mono(1,1-dimethylethyl)ester.

(d)
1-[N-[2-[2-(1,1-Dimethylethoxy)-2-oxoethyl]-1-oxo-4-phenylbutyl]-L-alanyl]-L-proline, (1,1-dimethylethyl)ester A mixture of 2-(2-phenylethyl)butanedioic acid, 4-mono(1,1-dimethylethyl)ester (600 mg., 2.16 mmole), L-alanyl-L-proline, 1,1-dimethylethyl ester (570 mg., 2.2 mmole), dicyclohexylcarbodiimide (460 mg., 2.2 mole) and 1-hydrobenzotriazole hydrate (300 mg., 2.2 mmole) in tetrahydrofuran (50 ml.) is stirred at 25° for 24 hours. The mixture is then concentrated and the residue dissolved in ethyl acetate. The solution is washed sequentially with 1N hydrochloric acid and 10% sodium bicarbonate, dried, and concentrated. The residue is dissolved in ether, filtered, and reconstituted to give a pale yellow oil which is filtered through Florisil (1:1, hexane:ethyl acetate) and reconcentrated to give 600 mg., of 1-[N-[2-[2-(1,1-dimethylethoxy)-2-oxoethyl]-1-oxo-4-phenylbutyl]-L-alanyl]-L-proline, (1,1-dimethylethyl)ester as a colorless oil.

(e)
1-[N-[2-(Carboxymethyl)-1-oxo-4-phenylbutyl]-L-alanyl]-L-proline (isomer A) and (isomer B)

A solution of the (1,1-dimethylethyl)ester product from part (d) (600 mg., 1.2 mmole) in trifluoroacetic acid is stirred at 25° for 2 hours, after which it is concentrated by rotary evaporation. Toluene is added and the mixture is reconcentrated. The residue is dissolved in 1N lithium hydroxide(1 mol.eq.) and passed through a column of AG50(Li+), eluting with water. The mixture is concentrated and chromatographed on HP-20, eluting with water. Fractions are monitored by TLC (20:45:6:11, pyridine: ethyl acetate:acetic acid:water) giving two products:

200 mg. of 1-[N-[2-(carboxymethyl)-1-oxo-4-phenyl-butyl]-L-alanyl]-L-proline (isomer A); m.p. greater than 220°. TLC ($R_f$ 0.70 silica gel; 20:45:6:11, pyridine:ethyl acetate:acetic acid:water). $[\alpha]_D = -64°$ (c =1,water)

Anal. Calc'd. for $C_{20}H_{24}N_2O_6Li_2 \cdot 2.37\ H_2O$:
C, 53,98; H, 6.51; N, 6.29.
Found: C, 53.98; H, 6.40; N, 6.19.

150 mg. of 1-[N-[2-(carboxymethyl)-1-oxo-4-phenyl-butyl]-L-alanyl]-L-proline (isomer B); m.p. greater than 220°. TLC ($R_f$ 0.63 silica gel; 20:45:6:11, pyridine:ethyl acetate:acetic acid:water). $[\alpha]_D = -85°$ (c =1, water).

Anal Calc'd for $C_{20}H_{24}N_2O_6Li_2 \cdot 1.84\ H_2O$:
C, 55.17; H, 6.41; N, 6.43.
Found: C,55.17; H, 6.21; N, 6.40.

EXAMPLE 8
(±)-1-[N-(3-Hydroxy-3-carboxy-1-oxopropyl)-L-alanyl]-L-proline, dilithium salt (a)
(±)-1-[N-[3-(Acetyloxy)-4-ethoxy-1,4-dioxobutyl]-L-alanyl]-L-proline, phenylmethyl ester A mixture of 2-(acetyloxy)butanedioic acid, 1-monoethyl ester (2.5 g., 5.4 mmole) [prepared as described in JACS, Vol. 88, p. 5306 (1966)], L-alanyl-L-proline, phenylmethyl ester, tosylate salt (5.0 g., 11.2 mmole), diisopropylamine (2.0 ml., 11.2 mmole), dicyclohexyl-carbodiimide (2.3 g., 11.2 mmole), and 1-hydroxybenzo-triazole hydrate (1.5 g., 11.2 mmole) in tetrahydrofuran (100 ml.) is stirred at 25° for 18 hours, after which it is filtered and concentrated. The residue is dissolved in ethyl acetate and the solution is washed sequentially with 1N hydrochloric acid and 10% aqueous sodium bicarbonate, dried, and concentrated. The residue is dissolved in ether, filtered and reconcentrated to give 4.0 g. of (±)-1-[N-[3-(acetyloxy)-4-ethoxy-1,4-dioxobutyl]-L-alanyl]-L-proline, phenylmethyl ester.

(b)
(±)-1-[N-(3-Hydroxy-3-carboxy-1-oxopropyl)-L-alanyl]-L-proline, dilithium salt A mixture of the phenylmethyl ester product from part (a) (2.5 g., 5.4 mmole), 1N aqueous lithium hydroxide (20 ml.,20 mmole) and ethanol (20 ml.) is stirred at 25° for 45 hours, after which it is diluted with water and washed with ether. The aqueous layer is passed through a column of excess AG50 (Li+) and concentrated to give 1.4 g. of the lithium salt as an orange glass which is not homogeneous. The salt is reprotonated with excess AG50 (H+) (column) and chromatographed as the free acid on HP-20 (water to ethanol gradient). Fractions containing the major product are combined and concentrated. The residue is dissolved in water, passed through a column of excess AG50 (Li+), and lyophilized to give 350 mg. of (±)-1-[N-(3-hydroxy-3-carboxy-1-oxopropyl)-L-alanyl]-L-proline, dilithium salt; m.p. 230°-250° (dec.). TLC ($R_f$ 0.45 silica gel; n-butanol:acetic acid:ethyl acetate:water, 1:1:1:1). $[\alpha]_D^{20} = -104°$ (c =2, water).

Anal. Calc'd. for $C_{12}H_{16}N_2O_7Li_2 \cdot 1.6\ H_2O$:
C, 41.90; H, 5.57; N, 8.14.
Found: C, 41.90; H, 5.64; N, 8.08.

EXAMPLE 9
D,L-1-[N-[N-Benzoyl-α-(phenylmethyl)aspartyl]-L-alanyl]-L-proline (a) 2-Phenyl-4-(phenylmethyl)-5(4H)-oxazolone To a stirred, cold (0°) suspension of N-benzoyl-D,L-phenylalanine (53.8 g., 0.2 mole) in tetrahydrofuran (400 ml.) is added a solution of dicyclohexylcarbodiimide (45.5 g., 0.22 mole) in tetrahydrofuran (200 ml.) over a 30 minute period. After stirring overnight (0°→26°), the reaction mixture is filtered, the filtrate concentrated in vacuo, and the residue redissolved in ether (100 ml.), filtered again and finally concentrated in vacuo into an oily residue. Trituration with isopropyl ether affords 50.2 g. of 2-phenyl-4-(phenylmethyl)-5(4H)-oxazolone as a white solid.

(b)
4,5-Dihydro-5-oxo-2-phenyl-4-(phenylmethyl)-4-oxazoleacetic acid, 1,1-dimethylethyl ester To a cold solution of 2-phenyl-4-(phenylmethyl)-5(4H)-oxazolone (10.4 g., 40 mmole) in dimethylformamide (40 ml.) is added diisopropylethylamine (11.2 ml., 80 mmole) followed by the dropwise addition of tert-butylbromoacetate (12.9 ml., 80 mmole). After stirring overnight (0°→26°), the reaction mixture is poured into water (400 ml.) and extracted with ether (4×200 ml.). The organic extracts are washed with water (5 times), dried (MgSO4) and concentrated in vacuo to an oily residue (16.5 g.). This crude product is chromatographed on silica gel (5% hexane, methylene chloride) to give 7.6 g. of 4,5-dihydro-5-oxo-2-phenyl-4-(phenylmethyl)-4-oxazoleacetic acid, 1,1-dimethylethyl ester as a white solid.

(c)
(±)-1-[N-[2-(Benzoylamino)-4-(1,1-dimethylethoxy)-1,4-dioxo-(2-phenylmethyl)butyl]-L-alanyl]-L-proline, 1,1-dimethylethyl ester A solution of 4,5-dihydro-5-oxo-2-phenyl-4-(phenylmethyl)-4-oxazoleacetic acid, 1,1-dimethyl-ethyl ester (3 g., 8.21 mmole) and L-alanyl-L-proline, 1,1-dimethylethyl ester (1.99 g., 8.21 mmole) in tetrahydrofuran (150 ml.) is heated under reflux overnight. The reaction mixture is concentrated in vacuo to an oily residue (5 g.). This crude product is chromatographed on silica gel (1% methanol, methylene chloride) to give 2.6 g. of (±)-1-[N-[2-(benzoylamino)-4-(1,1-dimethylethoxy)-1,4-dioxo-2-(phenylmethyl)butyl]-L-alanyl]-L-proline, 1,1-dimethylethyl ester as a white solid.

(d)
D,L-1-[N-[N-Benzoyl-α-(phenylmethyl)aspartyl]-L-alanyl]-L-proline

The tert-butyl ester product from part (c) (2.5 g., 4.11 mmole) is added to distilled trifluoroacetic acid (10 ml.) containing anisole (1 ml.). After two hours the volatiles are removed in vacuo, and the residue chased with toluene (two times). After trituration with ether (two times), 0.37 g. of D,L-1-[N-[N-benzoyl-α-(phenylmethyl)aspartyl]-L-alanyl]-L-proline are obtained as white solids. TLC (R$_f$0.77 silica gel, n-butanol:acetic acid:water, 3:1:1).

Anal. Calc'd. for $C_{26}H_{29}N_3O_7 \cdot 1.3\ H_2O$:
C, 60.13; H, 6.14; N, 8.09.
Found: C, 60.13; H, 5.63; N, 7.99.

EXAMPLE 10

L-Aspartyl-L-alanyl-L-proline, dilithium salt (a)

1-[N-L-[2-[[(1,1-Dimethylethoxy)carbonyl]amino]-1,4-dioxo-4-(phenylmethoxy)-butyl]-L-alanyl]-L-proline, phenylmethyl ester To a suspension of L-2-[[(1,1-dimethylethoxy)carbonyl]amino]-1,4-butanedioic acid, 4-mono(phenylmethyl) ester (5.0 g., 15.5 mmole) and L-alanyl-L-proline, phenylmethyl ester, tosylate salt (6.9 g., 15.5 mmole) in tetrahydrofuran (150 ml.) are added diisopropylethylamine (2.8 ml., 15.5 mmole), dicyclohexylcarbodiimide (3.2 g., 15.5 mmole) and 1-hydroxybenzotriazole hydrate (2.0 g., 15.5 mmole). The resulting mixture is stirred at 25° for 17 hours, after which it is filtered and concentrated by rotary evaporation. The residue is taken up in ethyl acetate, filtered, washed sequentially with 1N hydrochloric acid and 10% sodium bicarbonate solution, dried, and concentrated to give 7.9 g. of 1-[N-L-[2-[[(1,1-dimethylethoxy)carbonyl]amino]-1,4-dioxo-4-(phenylmethoxy)-butyl]-L-alanyl]-L-proline, phenylmethyl ester. TLC (R$_f$0.8 silica gel, ethyl acetate).

(b)

1-[N-L-[2-Amino-1,4-dioxo-4-(phenylmethoxy)-butyl]-L-alanyl]-L-proline, phenylmethyl ester A solution of the phenylmethyl ester product from part (a) (7.9 g., 13.6 mmole) in trifluoroacetic acid (50 ml., distilled from phosphorus pentoxide) is stirred at 25° for two hours, after which it is concentrated by rotary evaporation. The residue is dissolved in ethyl acetate, washed with 10% aqueous sodium bicarbonate, dried, and reconcentrated to give 6.0 g. of 1-[N-L-[2-amino-1,4-dioxo-4-(phenylmethoxy)-butyl]-L-alanyl]-L-proline, phenylmethyl ester as a pale yellow oil.

(c) L-Aspartyl-L-alanyl-L-proline, dilithium salt

A solution of the phenylmethyl ester product from part (b) (1.6 g., 3.3 mmole) in ethanol (200 ml.) is hydrogenated with palladium on carbon catalyst (200 mg.) on a Parr apparatus at 50 psi for 18 hours, after which it is filtered and concentrated. This material is redissolved in a mixture of ethanol (100 ml.) and methanol (100 ml.), fresh catalyst (200 mg.) is added, and the mixture is hydrogenated at 40 psi for 16 additional hours. The mixture is then filtered and concentrated to give an off-white solid which is chromatographed on HP-20 (water to ethanol gradient). Fractions containing the major product are combined and passed through a column of AG50WX2 (Li+). The resulting solution is lyophilized to give 425 mg. of L-aspartyl-L-alanyl-L-proline, dilithium salt as a glassy solid. TLC (R$_f$ 0.4 silica gel, n-butanol:acetic acid:ethyl acetate:water, 1:1:1:1). [α]$_D$= −60° (c =1, water).

Anal Calc'd. for $C_{12}H_{17}N_3O_6Li_2 \cdot 2H_2O$:
C, 41.27; H, 6.06; N, 12.03; Li, 3.97.
Found: C, 41.17; H, 6.38; N, 12.10; Li, 4.02.

EXAMPLE 11

1-[N-(N-Benzoyl-L-aspartyl)-L-alanyl]-L-proline (a)

1-[N-L-[2-(Benzoylamino)-1,4-dioxo-4-(phenylmethoxy)-butyl]-L-alanyl]-L-proline, phenylmethyl ester A mixture of 1-[N-L-[2-Amino-1,4-dioxo-4-(phenylmethoxy)-butyl]-L-alanyl]-L-proline, phenylmethyl ester (4.3 g., 9.1 mmole) [prepared as described in Example 10(b)], ethyl acetate (75 ml.), water (75 ml.), sodium bicarbonate (10 g.), and benzoyl chloride (1.2 ml., 10.4 mmole) is stirred at 25° for 19 hours, after which it is filtered and transferred to a separatory funnel. The aqueous layer is drawn off and the organic phase is washed with 10% aqueous sodium bicarbonate and with 5% potassium bisulfate, dried and concentrated. The residue (1.5 g.) is flash chromatographed on LP-1 (hexane to ethyl acetate gradient) to give 750 mg. of 1-[N-L-[2-(benzoylamino)-1,4-dioxo-4-(phenylmethoxy)-butyl]-L-alanyl]-L-proline, phenylmethyl ester as a white solid; m.p. 162°–163°.

(b) 1-[N-(N-Benzoyl-L-aspartyl)-L-alanyl]-L-proline

A mixture of the phenylmethyl ester product from part (a) (700 mg., 1.19 mmole), 10% palladium on carbon catalyst (200 mg.), ethanol (200 ml.), methanol (50 ml.), and ethyl acetate (50 ml.) is hydrogenated in a Parr apparatus at 40 psi for 17 hours, after which it is filtered and concentrated. The residue is dissolved in methanol and precipitated by the addition of ether to give 330 mg. of 1-[N-(N-benzoyl-L-aspartyl)-L-alanyl]-L-proline; decomposition above 100°. TLC (R$_f$ 0.25 silica gel, ethyl acetate:pyridine:acetic acid:water, 45:20:6:11). [α]$_D$= −94° (c=0.5, water).

Anal Calc'd. for $C_{19}H_{23}N_3O_7 \cdot 1.4\ H_2O$: C, 53.01; H, 6.04; N, 9.76. Found: C, 53.01; H, 5.71; N, 9.60.

EXAMPLE 12

1-[N-(D-Aspartyl)-L-alanyl]-L-proline (a)

1-[N-D-[2-[[(1,1-Dimethylethoxy)carbonyl]amino]-1,4-dioxo-4-(phenylmethoxy)-butyl]-L-alanyl]-L-proline, phenylmethyl ester To a suspension of D-2-[[(1,1-dimethylethoxy)carbonyl]amino]-1,4-butanedioic acid, 4-mono(phenylmethyl) ester (5.0 g., 15.5 mmole) and L-alanyl-L-proline, phenylmethyl ester tosylate salt (6.3 g., 14.1 mmole) in tetrahydrofuran (125 ml.) are added 1-hydroxybenzotriazole hydrate (1.9 g., 14.1 mmole), dicyclohexylcarbodiimide (2.9 g., 14.1 mmole) and diisopropylethylamine (2.4 ml., 14.1 mmole). The resulting solution is stirred at room temperature overnight, after which it is filtered, concentrated, dissolved in ethyl acetate and washed sequentially with 1N hydrochloric acid and 10% sodium bicarbonate solution. The ethyl acetate layer is then dried (MgSO$_4$) and concentrated. The residue is dissolved in ether and millipore filtered to remove residual dicyclohexylurea. The filtrate is concentrated to give 8.2 g. of 1-[N-D-[2-[[(1,1-dimethylethoxy)carbonyl]amino]-1,4-dioxo-4-(phenylmethoxy)-butyl]-L-alanyl]-L-proline, phenylmethyl ester as a clear oil. TLC (R$_f$=0.6 silica gel, ethyl acetate).

(b) 1-[N-D-[2-Amino-1,4-dioxo-4-(phenylmethoxy)butyl]-L-alanyl]-L-proline, phenylmethyl ester The phenylmethyl ester product from part (a) (8.2 g., 14.1 mmole) is treated with trifluoroacetic acid (50 ml.) according to the procedure of Example 10(b) to yield 5.1 g. of 1-[N-D-[2-amino-1,4-dioxo-4-(phenylmethoxy)butyl]-L-alanyl]-L-proline, phenylmethyl ester as a pale yellow oil. TLC ($R_f$ 0.51 silica gel; ethyl acetate:-methanol, 1:1).

(c) 1-[N-(D-Aspartyl-L-alanyl]-L-proline

A solution of the phenylmethyl ester product from part (b) (900 mg., 1.8 mmole) in ethanol (125 ml.) is added to a suspension of 10% palladium on carbon catalyst (120 mg.) in ethanol (75 ml.). The solution is hydrogenated on a Parr apparatus at 30 psi for 17 hours. The solution is then filtered and concentrated to give a white solid. The residue is applied to an HP-20 column and eluted with a water to ethanol gradient. Fractions containing the desired product are combined and concentrated. The residue is dissolved in water and lyophilized to give 430 mg. of 1-[N-(D-aspartyl)-L-alanyl]-L-proline as a white powder; m.p. (145°) 170° (dec.). TLC ($R_f$ 0.35 silica gel, n-butanol:acetic acid:water:ethyl acetate; 1:1:1:1). $[\alpha]_D = -164°$ (c=0.8, water).

Anal. Calc'd. for $C_{12}H_{19}N_3O_6 \cdot 0.85\ H_2O$: C, 45.52; H, 6.59; N, 13.27. Found: C, 45.76; H, 6.42; N, 12.89.

EXAMPLE 13

1-[N-(N-Benzoyl-D-aspartyl)-L-alanyl]-L-proline

(a) 1-[N-D-[2-(Benzoylamino)-1,4-dioxo-4-(phenylmethoxy)-butyl]-L-alanyl]-L-proline, phenylmethyl ester To a stirring solution 1-[N-D-[2-amino-1,4-dioxo-4-(phenylmethoxy)-butyl]-L-alanyl]-L-proline, phenylmethyl ester (2.0 g., 4.2 mmole) [prepared as described in Example 12 (b)], in tetrahydrofuran are added benzoyl chloride (0.48 ml., 4.2 mmole) and diisopropylethylamine (0.73 ml., 4.2 mmole). The resulting solution is stirred for 46 hours, after which it is filtered through Celite and concentrated. The pale yellow oil begins to crystallize upon addition of ethanol. The crude product is recrystallized from ethanol to give 1.9 g. of 1-[N-D-[2-(benzoylamino)-1,4-dioxo-4-(phenylmethoxy)-butyl]-L-alanyl]-L-proline, phenylmethyl ester as a white solid; m.p. 148°-149°.

(b) 1-[N-(N-Benzoyl-D-aspartyl)-L-alanyl]-L-proline

A solution of the phenylmethyl ester product from part (a) (1.7 g., 2.9 mmole) in ethanol (200 ml.) and 10% palladium on carbon catalyst (200 mg.) are combined and hydrogenated on a Parr apparatus for 18 hours at 40 psi. The resulting solution is filtered and concentrated. The residue is dissolved in water, millipore filtered and concentrated. The concentrate is dissolved in 10% sodium bicarbonate solution, washed with ether, acidified with concentrated hydrochloric acid and extracted with ether and ethyl acetate. The extracts are combined and concentrated. The residue is chromatographed on HP-20 eluting with a gradient of water to ethanol. Fractions containing the desired product are combined and concentrated to give a white solid which is recrystallized from acetone to yield 300 mg. of 1-[N-(N-benzoyl-D-aspartyl)-L-alanyl]-L-proline; m.p. 161°-163°. TLC ($R_f$ 0.68 silica gel; n-butanol:acetic acid:water:ethyl acetate; 1:1:1:1). $[\alpha]_D = -121°$ (c=0.33, water).

Anal. Calc'd. for $C_{19}H_{23}N_3O_7$: C, 56.29; H, 5.72; N, 10.36. Found: C, 56.13; H, 5.79; N, 10.25.

EXAMPLE 14

1-[N-(L-β-Aspartyl)-L-alanyl]-L-proline

(a) 1-[N-L-[3-[[(1,1-Dimethylethoxy)carbonyl]amino]-1,4-dioxo-4-(phenylmethoxy)-butyl]-L-alanyl]-L-proline, phenylmethyl ester To a mixture of L-3-[[(1,1-dimethylethoxy)carbonyl]amino]-1,4-butanedioic acid, 4-mono(phenylmethyl) ester (3.4 g., 10.5 mmole) and L-alanyl-L-proline, phenylmethyl ester, tosylate salt (5.0 g., 11 mmole) in tetrahydrofuran (100 ml.) are added diisopropylethylamine (2.0 ml., 11 mmole), 1-hydrobenzotriazole hydrate (1.5 g., 11 mmole), and dicyclohexylcarbodiimide (2.3 g., 11 mmole). The mixture is stirred at 25° for 17 hours, after which it is filtered and concentrated by rotary evaporation. The residue is dissolved in ethyl acetate and the solution is washed sequentially with 1N hydrochloric acid and 10% aqueous sodium bicarbonate, dried, and concentrated. The residue is dissolved in ether, filtered, and reconcentrated to give 7.0 g. of crude 1-[N-L-[3-[[(1,1-dimethylethoxy)carbonyl]amino]-1,4-dioxo-4-(phenylmethoxy)butyl]-L-alanyl]-L-proline, phenylmethyl ester.

(b) 1-[N-L-[3-Amino-1,4-dioxo-4-(phenylmethoxy)butyl]-L-alanyl]-L-proline, phenylmethyl ester A solution of the phenylmethyl ester product from part (a) (7.0 g.) in trifluoroacetic acid (50 ml.) is stirred at 25° for 2 hours. The mixture is then concentrated by rotary evaporation. The residue is dissolved in ethyl acetate and the solution is washed with 10% aqueous sodium bicarbonate, dried, and reconcentrated to give 4.6 g. of a pale yellow oil. Chromatography of a portion of this material (3.9 g.) on LP-1 (ethyl acetate to 3:1 ethyl acetate:methanol gradient) gives 2.5 g. of pure 1-[N-L-[3-amino-1,4-dioxo-4-(phenylmethoxy)-butyl]-L-alanyl]-L-proline, phenylmethyl ester.

(c) 1-[N-(L-β-Aspartyl)-L-alanyl]-L-proline

A mixture of the phenylmethyl ester product from part (b) (900 mg., 1.87 mmole) and 10% palladium on carbon catalyst (250 mg.) in ethanol (200 ml.) is hydrogenated on a Parr apparatus at 50 psi for 17 hours, after which it is filtered and concentrated. The residue is dissolved in water and passed through a column of AG50WX2 (Li+). The solution is reconcentrated and the residue is chromatographed on HP-20 (eluting with water). The major fraction is concentrated to give a yellow glass. This material is chromatographed on AG50WX2 (H+), eluting first with water then with 5% pyridine in water. A yellow material is eluted first (ninhydrin-negative), followed by a colorless material (ninhydrin-positive). The ninhydrin-positive fractions are concentrated and lyophilized to give 150 mg. of 1-[N-(L-β-aspartyl)-L-alanyl]-L-proline. TLC ($R_f$ 0.35 silica gel; n-butanol:acetic acid:ethyl acetate:water; 1:1:1:1). $[\alpha]_D = -127°$ (c=0.5, water).

Anal. Calc'd. for $C_{12}H_{19}N_3O_6 \cdot 0.65\ H_2O$: C, 46.05; H, 6.54; N, 13.93. Found: C, 46.05; H, 6.54; N, 13.34.

EXAMPLE 15

1-[N-(N-Benzoyl-L-β-aspartyl)-L-alanyl]-L-proline (a)

1-[N-L-[3-(Benzoylamino)-1,4-dioxo-4-(phenylmethoxy)-butyl]-L-alanyl]-L-proline, phenylmethyl ester To a solution of 1-[N-L-[3-amino-1,4-dioxo-4-(phenylmethoxy)-butyl]-L-alanyl]-L-proline, phenylmethyl ester (1.8 g., 3.75 mmole) [prepared as set forth in Example 14(b)] in tetrahydrofuran (50 ml.) are added diisopropylethylamine (6.65 ml., 3.75 mmole) and benzoyl chloride (4.35 ml., 3.75 mmole). The resulting mixture is stirred at 25° for 24 hours, after which it is concentrated by rotary evaporation. The residue is dissolved in ethyl acetate, washed sequentially with 1N hydrochloric acid and 10% aqueous sodium bicarbonate, dried, and concentrated to give 2.5 g. of a dark oil. Rapid chromatography on Florisil (hexane to ethyl acetate gradient) gives 1.0 g. of 1-[N-L-[3-(benzoylamino)-1,4-dioxo-4-(phenylmethoxy)-butyl]-L-alanyl]-L-proline, phenylmethyl ester as the major product. TLC ($R_f$ 0.6 silica gel, ethyl acetate).

(b) 1-[N-(N-Benzoyl-L-β-aspartyl)-L-alanyl]-L-proline

A mixture of the phenylmethyl ester product from part (a) (1.0 g., 1.7 mmole), 10% palladium on carbon catalyst (150 mg.), ethyl acetate (75 ml.), and ethanol (75 ml.) is hydrogenated on a Parr apparatus at 40 psi for 18 hours, after which it is filtered and concentrated. The residue is chromatographed on HP-20 (water to ethanol gradient) and the major product is lyophilized to give 600 mg. of 1-[N-(N-benzoyl-L-β-aspartyl)-L-alanyl]-L-proline as a white solid; m.p. 115°–125°. TLC ($R_f$ 0.7 silica gel, n-butanol:acetic acid:ethyl acetate:water; 1:1:1:1). $[\alpha]_D = -96°$ (c=1, water).

Anal. Calc'd. for $C_{19}H_{23}N_3O_7 \cdot 0.56\ H_2O$: C, 54.93; H, 5.85; N, 10.11. Found: C, 54.93; H, 5.72; N, 10.19.

EXAMPLE 16

1-[N-(D-β-Aspartyl)-L-alanyl]-L-proline (a)

1-[N-D-[3-[[(1,1-Dimethylethoxy)carbonyl]amino]-1,4-dioxo-4-(phenylmethoxy)-butyl]-L-alanyl]-L-proline, phenylmethyl ester To a suspension of D-3-[[(1,1-dimethylethoxy)carbonyl]amino]-1,4-butanedioic acid, 4-mono(phenylmethyl) ester (3.62 g., 11.2 mmole) [prepared as described in J. Med. Chem., Vol. 16, p. 624 (1973)] and L-alanyl-L-proline, phenylmethyl ester, tosylate salt (5.0 g., 11.2 mmole) are added dicyclohexylcarbodiimide (2.3 g., 11.2 mmole), 1-hydroxybenzotriazole hydrate (1.5 g., 11.2 mmole) and diisopropylethylamine (2 ml., 11.2 mmole). The resulting mixture is stirred at room temperature for 18 hours, after which it is filtered through Celite and concentrated. The residue is dissolved in ethyl acetate, washed sequentially with 1N hydrochloric acid and 10% sodium bicarbonate, dried (MgSO$_4$) and concentrated. The residue is taken up in ether, filtered and concentrated to give 1-[N-D-[3-[[(1,1-dimethylethoxy)carbonyl]amino]-1,4-dioxo-4-(phenylmethoxy)butyl]-L-alanyl]-L-proline, phenylmethyl ester.

(b)

1-[N-D-[3-Amino-1,4-dioxo-4-(phenylmethoxy)butyl]-L-alanyl]-L-proline, phenylmethyl ester A solution of the phenylmethyl ester product from part (a) (6.5 g., 11.2 mmole) in trifluoroacetic acid (50 ml.) is stirred at room temperature for one hour. The resulting solution is concentrated, dissolved in ethyl acetate and washed with 10% sodium bicarbonate. The ethyl acetate layer is dried (MgSO$_4$) and concentrated to give 5.4 g. of 1-[N-D-[3-amino-1,4-dioxo-4-(phenylmethoxy)-butyl]-L-alanyl]-L-proline, phenylmethyl ester.

(c) 1-[N-(D-β-Aspartyl)-L-alanyl]-L-proline

A mixture of the phenylmethyl ester product from part (b) (1.5 g., 3.1 mmole) and 10% palladium on carbon catalyst (250 mg.) in ethanol (200 ml.) is hydrogenated on the Parr apparatus at 30 psi for 15 hours. The resulting solution is filtered and concentrated. The crude residue is chromatographed on HP-20 using a gradient elution of water to acetonitrile. Fractions containing the desired product (TLC) are combined and concentrated. This material is chromatographed again on HP-20 using a water to 20% aqueous ethanol elution gradient. Those fractions containing the desired material are combined, concentrated, and the residue is dissolved in water, and lyophilized to give 220 mg. of 1-[N-(D-β-aspartyl)-L-alanyl]-L-proline; m.p. 174°–179° (dec.). TLC ($R_f$ 0.36 silica gel, n-butanol:acetic acid:water:ethyl acetate; 1:1:1:1). $[\alpha]_D = -81°$ (c=0.62, water).

Anal. Calc'd. for $C_{12}H_{19}N_3O_6 \cdot 0.84\ H_2O$: C, 45.54; H, 6.59; N, 13.28. Found: C, 45.54; H, 6.38; N, 12.89.

EXAMPLE 17

1-[N-(N-Benzoyl-D-β-aspartyl)-L-alanyl]-L-proline (a)

1-[N-D-[3-(Benzoylamino)-1,4-dioxo-4-(phenylmethoxy)-butyl]-L-alanyl-L-proline, phenylmethyl ester A solution of 1-[N-D-[3-amino-1,4-dioxo-4-(phenylmethoxy)-butyl]-L-alanyl]-L-proline, phenylmethyl ester (4.0 g., 8.3 mmole) [prepared as set forth in Example 16(b)], diisopropylethylamine (1.4 ml., 8.3 mmole), and benzoyl chloride (1.2 g., 8.3 mmole) in tetrahydrofuran (100 ml., distilled) is stirred at room temperature for 2 days. The resulting solution is filtered through Celite and concentrated to give a yellow oil. The residue is chromatographed on LP-1 using an elution gradient of ethyl acetate: hexane (1:1 to 5:3). Fractions are monitored by TLC (silica gel, ethyl acetate) and those containing the desired material ($R_f$ 0.47) are combined and concentrated to give 3.2 g. of 1-[N-D-[3-(benzoylamino)-1,4-dioxo-4-(phenylmethyl)-butyl]-L-alanyl]-L-proline, phenylmethyl ester as an oil.

(b)

1-[N-(N-Benzoyl-D-β-Aspartyl)-L-alanyl]-L-proline

A solution of the phenylmethyl ester from part (a) (2.2 g., 3.6 mmole) and 10% palladium on carbon catalyst in ethanol is hydrogenated on a Parr apparatus at 30 psi for 17 hours. The resulting solution is filtered through Celite and concentrated to give a yellow foam. The residue is triturated with ether and dried. The material is chromatographed on HP-20 using a water to ethanol gradient. Fractions containing the desired product are combined and concentrated. The residue is triturated with ether and dried to give 450 mg. of 1-[N-(N-(benzoyl-D-$\beta$-aspartyl)-L-alanyl]-L-proline as a white powder; m.p. 110°. TLC (R$_f$ 0.57 silica gel, n-butanol:acetic acid:water:ethyl acetate, 1:1:1:1). $[\alpha]_D = -63°$ (c=1.4, water).

Anal. Calc'd. for $C_{19}H_{23}N_3O_7 \cdot 0.3\ H_2O$: C, 55.51; H, 5.79; N, 10.22. Found: C, 55.51; H, 5.84; N, 10.05.

EXAMPLE 18

(cis)-1-[N-(2-Carboxycyclopropyl)carbonyl]-L-alanyl]-L-proline, dilithium salt (a) (cis)-1,2-Cyclopropanedicarboxylic acid, mono(phenylmethyl)ester A solution of (cis)-1,2-cyclopropanedicarboxylic anhydride (1.7 g., 15.2 mmole) [prepared according to the procedure set forth in JACS, Vol. 80, p. 6568 (1958); Method A] and diisopropylethylene (1 ml.) in benzyl alcohol (25 ml.) is stirred at room temperature for 24 hours. The resulting solution is diluted with 10% sodium bicarbonate solution and washed with ethyl acetate. The aqueous layer is acidified with concentrated hydrochloric acid and extracted with ether (2×100 ml.) and ethyl acetate (1×100 ml.). The extracts are combined, dried (MgSO$_4$) and concentrated to give 2.2 g. of (cis)-1,2-cyclopropanedicarboxylic acid, mono(phenylmethyl) ester as a white crystalline solid.

(b) (cis)-1-[N-(2-Carboxycyclopropyl)carbonyl]-L-alanyl]-L-proline, bis(phenylmethyl)ester To a stirring solution of (cis)-1,2-cyclopropanedicarboxylic acid, mono(phenylmethyl) ester (2.1 g., 9.5 mmole) and L-alanyl-L-proline, phenylmethyl ester tosylate salt (4.3 g., 9.5 mmole) in tetrahydrofuran are added dicyclohexylcarbodiimide (2.0 g., 9.5 mmole), diisopropylethylamine (1.65 ml., 9.5 mmole), and 1-hydroxybenzotriazole hydrate (1.3 g., 9.5 mmole). The reaction mixture is stirred at room temperature for 5 hours. It is then filtered, concentrated, dissolved in ethyl acetate and washed sequentially with 10% sodium bicarbonate solution and 1N hydrochloric acid. The solid is dried (MgSO$_4$), concentrated, dissolved in ether, filtered and concentrated. The product is chromatographed on LP-1 using an elution gradient of ethyl acetate:haxane (1:1) to ethyl acetate. Fractions containing the desired material (R$_f$ 0.27 silica gel, ethyl acetate) are combined and concentrated to give 2 g. of (cis)-1-[N-(2-carboxycyclopropyl)carbonyl]-L-alanyl]-L-proline, bis(phenylmethyl) ester as a colorless oil.

(c) (cis)-1-[N-(2-Carboxycyclopropyl)carbonyl]-L-alanyl]-L-proline, dilithium salt A solution of the phenylmethyl ester product from part (b) (2.0 g., 4.3 mmole) and 10% palladium on carbon catalyst in ethanol is hydrogenated on a Parr apparatus at 15 psi for 6 hours. The reaction mixture is filtered and concentrated. The residue is then dissolved in 5 ml. of 1N lithium hydroxide and washed with ether. The aqueous layer is applied to AG50WX2 resin (Li$^+$) and eluted with water. The acidic fractions are combined and concentrated to 1.2 g. of product as a clear glass. This material is dissolved in water and lyophilized to give (cis)-1-[N-(2-carboxycyclopropyl)carbonyl]-L-alanyl]-L-proline, dilithium salt as a granular solid; m.p. 235°–250°. TLC (R$_f$ 0.56 silica gel, n-butanol:acetic acid:water:ethyl acetate; 1:1:1:1). $[\alpha]_D = -113.3°$ (c=3.7, water).

Anal Calc'd. for $C_{13}H_{16}N_2O_6Li_2 \cdot 2.6\ H_2O$: C, 43.74; H, 5.99; N, 7.85. Found: C, 43.74; H, 5.64; N, 7.69.

EXAMPLE 19

(trans)-1-[N-[(2-Carboxycyclopropyl)carbonyl]-L-alanyl]-L-proline, dilithium salt (a) (trans)-1,2-Cyclopropanedicarboxylic acid, mono(diphenylmethyl)ester A solution of diphenyldiazomethane (7.5 g., 38.4 mmole) in ethyl acetate (50 ml.) is added to a stirring solution of trans-1,2-cyclopropanedicarboxylic acid (5.0 g., 38.4 mmole) [prepared as set forth in JACS, Vol. 80, p. 6568 (1958)]. The reaction mixture is stirred for 2 hours at room temperature, during which the dark purple color fades. The resulting solution is then extracted with 10% sodium bicarbonate solution (2×300 ml.). The combined extract is acidified with concentrated hydrochloric acid and extracted with ether (2×300 ml.). The ether extracts are dried (MgSO$_4$) and concentrated to give 6.1 g. of (trans)-1,2-cyclopropanedicarboxylic acid, mono(diphenylmethyl) ester as a white crystalline solid; m.p. 124°–127°.

(b) (trans)-1-[N-[[2-[(Diphenylmethoxy)carbonyl]cyclopropyl]carbonyl]-L-alanyl]-L-proline, phenylmethyl ester To a stirring solution of (trans)-1,2-cyclopropanedicarboxylic acid, mono(diphenylmethyl) ester (3.3 g., 11.2 mmole) in tetrahydrofuran are added L-alanyl-L-proline, phenylmethyl ester, tosylate salt (5.0 g., 11.2 mmole), dicyclohexylcarbodiimide (2.3 g., 11.2 mmole), 1-hydroxybenzotriazole hydrate (1.5 g., 11.2 mmole) and diisopropylethylamine (2 ml., 11.2 mmole). The resulting mixture is stirred at room temperature for 18 hours, then filtered through Celite and concentrated. The resulting residue is dissolved in ethyl acetate and washed sequentially with 1N hydrochloric acid and 10% sodium bicarbonate solution. The solution is then dried (MgSO$_4$) and concentrated to a pale yellow foam. The product is chromatographed on LP-1 eluting with hexane:ethyl acetate (1:1). Fractions containing the desired material (R$_f$ 0.6 silica gel, ethyl acetate) are combined and concentrated to give 3.8 g. of (trans)-1-[N-[[2-[(diphenylmethoxy)carbonyl]cyclopropyl]carbonyl]-L-alanyl]-L-proline, phenylmethyl ester as an oil.

(c) (trans)-1-[N-[(2-Carboxycyclopropyl)carbonyl]-L-alanyl]-L-proline, dilithium salt A solution of the phenylmethyl ester product from part (b) (1.8 g., 3.2 mmole) in ethanol (50 ml.) is added to a slurry of 10% palladium on carbon catalyst (200 mg.) in ethanol (75 ml.). The resulting mixture is stirred under a flow of hydrogen at room temperature for 4 hours. The reaction mixture is then filtered through Celite and concentrated. The residue is dissolved in 3 ml. of 1N lithium hydroxide and washed with ether. The aqueous solution is then applied to AG50WX2 resin (Li$^+$) and eluted with water. Fractions having a pH of 4–5 are combined and concentrated. The residue is then chromatographed on HP-20 using water as the eluant. Fractions containing the desired material are combined and concentrated. The residue is dissolved in water and lyophilized to give 350 mg. of (trans)-1-[N-[(2-carboxycyclopropyl)carbonyl]-L-alanyl]-L-proline, dilithium salt as a white solid; m.p. greater than 235°. TLC (R$_f$ 0.7 silica gel, n-butanol:acetic acid:water:ethyl acetate; 1:1:1:1). [α]$_D$= −109° (c=2, water).

Anal. Calc'd. for $C_{13}H_{16}N_2O_6Li_2 \cdot 2.11 H_2O$: C, 44.84; H, 5.85; N, 8.04. Found: C, 44.84; H, 6.06; N, 8.06.

EXAMPLE 20

(cis)-1-[N-[(2-Carboxycyclobutyl)carbonyl]-L-alanyl]-L-proline, dilithium salt (a) (cis)-1,2-Cyclobutanedicarboxylic acid, mono(phenylmethyl)ester (cis)-1,2-Cyclobutanedicarboxylic anhydride (10 g., 79.2 mmole) is dissolved in benzyl alcohol (50 ml.). To this solution is added diisopropylethylamine (1 ml.). The resulting solution is stirred at room temperature for 19 hours. The mixture is then poured into 10% sodium bicarbonate solution, washed with ethyl acetate, acidified with concentrated hydrochloric acid and extracted with ether. The combined ether extracts are dried (MgSO$_4$) and concentrated to give 16.2 g. of (cis)-1,2-cyclobutanedicarboxylic acid, mono(phenylmethyl) ester as a white crystalline solid; m.p. 66°–70°.

(b) (cis)-1-[N-[(2-Carboxycyclobutyl)carbonyl]-L-alanyl]-L-proline, bis(phenylmethyl)ester To a stirring solution of (cis)-1,2-cyclobutanedicarboxylic acid, mono(phenylmethyl) ester (2.6 g., 11.2 mmole) in tetrahydrofuran are added L-alanyl-L-proline, phenylmethyl ester tosylate salt (5.0 g., 11.2 mmole), dicyclohexylcarbodiimide (2.3 g., 11.2 mmole), 1-hydroxybenzotriazole hydrate (1.5 g., 11.2 mmole) and diisopropylethylamine (2.0 ml., 11.2 mmole). The resulting solution is stirred at room temperature for 22 hours. The mixture is then filtered, concentrated, redissolved in ethyl acetate and filtered again. The filtrate is washed with 10% sodium bicarbonate solution, 1N hydrochloric acid, and water. The ethyl acetate layer is dried (MgSO$_4$) and concentrated to give 5.2 g. of crude product. The crude material is chromatographed on an LP-1 column using an elution gradient of hexane:ethyl acetate (1:1) to ethyl acetate. Fractions containing the desired material (R$_f$ 0.2 silica gel, ethyl acetate) are combined and concentrated to give 1.9 g. of (cis)-1-[N-[(2-carboxycyclobutyl)carbonyl]-L-alanyl]-L-proline, bis(phenylmethyl)ester as a clear oil.

(c) (cis)-1-[N-[(2-Carboxycyclobutyl)carbonyl]-L-alanyl]-L-proline, dilithium salt A solution of the phenylmethyl ester product from part (b) (1.0 g., 2.0 mmole) in ethanol (80 ml.) is added to a slurry of 10% palladium on carbon catalyst (120 mg.) in ethanol (120 ml.). The resulting solution is purged with argon and hydrogenated in a Parr apparatus at 30 psi overnight. The resulting solution is filtered and concentrated to give 600 mg. of crude diacid product. This material is dissolved in 1N lithium hydroxide (3 ml.) and passed through an AG50WX2 (Li+) column eluting with water. Neutral fractions are combined and concentrated. The resulting material is chromatographed on an HP-20 column using water as eluant. Fractions containing the desired product are combined, concentrated, dissolved in water and lyophilized to give (cis)-1-[N-[(2-carboxycyclobutyl)carbonyl]-L-alanyl]-L-proline, dilithium salt as a white solid; m.p. greater than 110° (dec). TLC (R$_f$ 0.6 silica gel, n-butanol:acetic acid:water:ethyl acetate 1:1:1:1). [α]$_D$= −114° (c=1.4, methanol).

Anal. Calc'd. for $C_{14}H_{18}N_2O_6Li_2 \cdot 1.54 H_2O$: C, 47.78; H, 6.04; N, 7.96. Found: C, 47.78; H, 6.02; N, 7.83.

EXAMPLE 21

(trans)-1-[N-[(2-Carboxycyclobutyl)carbonyl]-L-alanyl]-L-proline, dilithium salt (a) (trans)-1,2-Cyclobutanedicarboxylic acid, mono(diphenylmethyl)ester To a stirring solution of (trans)-1,2-cyclobutanedicarboxylic acid (5 g., 34.7 mmole) in ethyl acetate (100 ml.) is added a solution of diphenyldiazomethane (6.7 g., 34.7 mmole) in ethyl acetate (50 ml.). The dark purple color of the diphenyldiazomethane solution fades to pale yellow within 45 minutes. The resulting solution is stirred an additional hour, after which it is extracted with 10% sodium bicarbonate solution (2×150 ml.). The combined extracts are acidified with concentrated hydrochloric acid and extracted with ether. The ether extracts are combined, dried (MgSO$_4$) and concentrated to give 3.4 g. of (trans)-1,2-cyclobutanedicarboxylic acid, mono (diphenylmethyl) ester as a white, crystalline solid; m.p. 57°–60°.

(b) (trans)-1-[N-[[2-[(Diphenylmethoxy)carbonyl]cyclobutyl]carbonyl]-L-alanyl]-L-proline, phenylmethyl ester To a stirring solution of (trans)-1,2-cyclobutanedicarboxylic acid, mono(diphenylmethyl) ester (3.4 g., 11.0 mmole) and L-alanyl-L-proline, phenylmethyl ester tosylate salt (6.2 g., 13.8 mmole) in tetrahydrofuran (125 ml.) are added 1-hydroxybenzotriazole hydrate (1.9 g., 13.8 mmole), dicyclohexylcarbodiimide (2.9 g., 13.8 mmole) and diisopropylethylamine (2.4 ml., 13.8 mmole). The resulting mixture is stirred at room temperature for 22 hours, after which is it filtered and concentrated. The residue is dissolved in ethyl acetate and washed sequentially with 1N hydrochloric acid and 10% sodium bicarbonate solution, dried MgSO$_4$, and concentrated. The resulting oil is applied to an LP-1 column and eluted with a gradient of hexane:ethyl acetate (1:1) to ethyl acetate. Fractions containing the desired product (R$_f$=0.5 silica gel, ethyl acetate) are combined and concentrated to give 2.45 g. of (trans)-1-[N-[[2-[(diphenylmethoxy)carbonyl]cyclobutyl]carbonyl]-L-alanyl]-L-proline, phenylmethyl ester as a clear oil.

(c) (trans)-1-N-[(2-Carboxycyclobutyl)carbonyl]-L-alanyl]-L-proline, dilithium salt A solution of the phenylmethyl ester product from part (b) (2.45 g., 4.3 mmole) in ethanol (50 ml.) is added to a suspension of 10% palladium on carbon catalyst (260 mg.) in ethanol (100 ml.) and placed on the Parr apparatus at 30 psi for 18 hours. The resulting solution is filtered through Celite, concentrated, and dissolved in 1N lithium hydroxide (4 ml.). The aqueous solution is washed with ether (1×10 ml.) and applied to an AG50WX2 (Li+) column, eluting with water. The fractions having a pH of approximately 4 are combined and concentrated. The residue is applied to a HP-20 column and eluted with water. Fractions containing the desired product are combined, concentrated, redissolved in water and lyophilized to give 590 mg. of (trans)-1-[N-[(2-carboxycyclobutyl)carbonyl]-L-alanyl]-L-proline, dilithium salt as a white solid; m.p. greater than 230°. TLC ($R_f$ 0.68 silica gel, n-butanol:acetic acid:water:ethyl acetate; 1:1:1:1). $[\alpha]_D = -88°$ (c=1.7, methanol).

Anal. Calc'd. for $C_{14}H_{18}N_2O_6Li_2 \cdot 1.5\ H_2O$: C, 47.88; H, 6.02; N, 7.98. Found: C, 48.01; H, 6.06; N, 7.90.

EXAMPLE 22

(cis)-1-[N-[(2-Carboxycyclopentyl)carbonyl]-L-alanyl]-L-proline, dilithium salt (a) (cis)-1,2-Cyclopentanedicarboxylic anhydride (cis)-1,2-Cyclopentanedicarboxylic acid (3.8 g., 24.0 mmole) [prepared according to the procedure set forth in JACS, Vol. 80, p. 6568 (1958)] is dissolved in acetyl chloride (35 ml.) and refluxed for 2 hours. The excess acetyl chloride is then removed in vacuo, and the residue is Kugelrohr distilled (1.5 mm. at 170°) to give a clear, colorless liquid which solidifies upon cooling. The product is crystallized from ether to give 2.75 g. of (cis)-1,2-cyclopentanedicarboxylic anhydride as a white, crystalline solid; m.p. 63°-68°.

(b) (cis)-1,2-Cyclopentanedicarboxylic acid, mono(phenylmethyl)ester

To a stirring solution of (cis)-1,2-cyclopentanedicarboxylic anhydride (2.3 g., 16.5 mmole) in benzyl alcohol (50 ml.) is added diisopropylethylamine (1 ml.). The resulting solution is stirred for 21 hours. The mixture is then poured into 10% sodium bicarbonate solution, washed with ethyl acetate, acidified with concentrated hydrochloric acid, and extracted with ether. The combined ether extracts are dried and concentrated to give 1.7 g. of (cis)-1,2-cyclopentanedicarboxylic acid, mono(phenylmethyl) ester.

(c) (cis)-1-[N-[(2-Carboxycyclopentyl)carbonyl]-L-alanyl]-L-proline, bis(phenylmethyl)ester To a stirring mixture of (cis)-1,2-cyclopentanedicarboxylic acid, mono(phenylmethyl) ester (1.7 g., 6.9 mmole) and L-alanyl-L-proline, phenylmethyl ester tosylate salt (3.1 g., 6.9 mmole) in tetrahydrofuran (200 ml.) are added 1-hydroxybenzotriazole hydrate (900 mg., 6.9 mmole), dicyclohexylcarbodiimide (1.4 g., 6.9 mmole) and diisopropylethylamine (1.2 ml., 6.9 mmole). The resulting solution is stirred for 19 hours at room temperature. The solution is then filtered through Celite and concentrated. The residue is dissolved in ethyl acetate and washed sequentially with 1N hydrochloric acid and 10% sodium bicarbonate solution. The ethyl acetate layer is then dried and concentrated. The residue is chromatographed on LP-1 using hexane:ethyl acetate (1:1) as eluant. Fractions containing the desired product ($R_f$ 0.47 silica gel, ethyl acetate) are combined and concentrated to give 2.5 g. of (cis)-1-[N-[(2-carboxycyclopentyl)carbonyl]-L-alanyl]-L-proline, bis(phenylmethyl)ester as an oil.

(d) (cis)-1-[N-[(2-Carboxycyclopentyl)carbonyl]-L-alanyl]-L-proline, dilithium salt A solution of the phenylmethyl ester product from part (c) (1.25 g., 2.5 mmole) in ethanol (50 ml.) is added to a slurry of 10% palladium on carbon catalyst (100 mg.) in ethanol (100 ml.). The resulting mixture is hydrogenated on the Parr apparatus at 30 psi for 4 hours. The solution is then filtered through Celite and concentrated. The residue is dissolved in 1N lithium hydroxide (3 ml.) and washed with ether. The aqueous solution is then applied to AG50WX2 (Li+) ion exchange resin and eluted with water. The neutral fractions are combined, concentrated, dissolved in water, and lyophilized to give 390 mg. of (cis)-1-[N-[(2-carboxycyclopentyl)carbonyl]-L-alanyl]-L-proline, dilithium salt; m.p. (210) 230° (dec.). TLC ($R_f$ 0.68 silica gel; n-butanol:acetic acid:ethyl acetate:water; 1:1:1:1). $[\alpha]_D = -118°$ (c=1.3, water).

Anal. Calc'd. for $C_{15}H_{20}N_2O_6Li_2 \cdot 1.79\ H_2O$: C, 48.62; H, 6.42; N, 7.56. Found: C, 48.62; H, 6.19; N, 7.55.

EXAMPLE 23

(trans)-1-[N-[(2-Carboxycyclopentyl)carbonyl]-L-alanyl]-L-proline, dilithium salt (a) (trans)-1,2-Cyclopentanedicarboxylic acid, mono(diphenylmethyl)ester To a stirring solution of (trans)-1,2-cyclopentanedicarboxylic acid (3 g., 18.9 mmole) in ethyl acetate (125 ml.) is added a solution of diphenyldiazomethane (3.7 g., 18.9 mmole) in ethyl acetate. The dark purple solution bubbles rapidly at first and then fades in color. The resulting solution is stirred at room temperature for 5 hours, then extracted with 10% sodium bicarbonate solution (3×200 ml.). The combined aqueous extracts are acidified with concentrated hydrochloric and extracted with ether. The ether extracts are combined, dried (MgSO4), and concentrated to give 4.1 g. of (trans)-1,2-cyclopentanedicarboxylic acid, mono(diphenylmethyl) ester as a pale yellow oil which solidifies at low temperature. TLC ($R_f$ 0.72 silica gel, ethyl acetate:methanol, 1:1).

(b) (trans)-1-[N-[[2-[(Diphenylmethoxy)carbonyl]cyclopentyl]carbonyl]-L-alanyl]-L-proline, phenylmethyl ester To a stirring solution of (trans)-1,2-cyclopentanedicarboxylic acid, mono(diphenylmethyl) ester (4.1 g., 12.6 mmole) and L-alanyl-L-proline, phenylmethyl ester tosylate salt (5.6 g., 12.6 mmole) in tetrahydrofuran (200 ml., distilled) are added dicyclohexylcarbodiimide (2.6 g., 12.6 mmole), 1-hydroxybenzotriazole hydrate (1.7 g., 12.6 mmole) and diisopropylethylamine (2.2 ml., 12.6 mmole). The resulting solution is stirred for 17 hours, then filtered through Celite and concentrated. The residue is dissolved in ethyl acetate and washed sequentially with 1N hydrochloric acid and 10% sodium bicarbonate. The solution is then dried (MgSO4), concentrated, dissolved in a minimum volume of ethyl acetate and filtered again. The final solution is concentrated to a yellow oil. The residue is chromatographed on LP-1 eluting with ethyl acetate:hexane (1:1). Fractions containing the desired product ($R_f$ 0.4 silica gel, ethyl acetate) are combined and concentrated to give 4.2 g. of (trans)-1-[N-[[2-[(diphenylmethoxy)carbonyl]cyclopentyl]carbonyl]-L-alanyl]-L-proline, phenylmethyl ester as a clear, colorless oil.

(c) (trans)-1-[N-[(2-Carboxycyclopentyl)carbonyl]-L-alanyl]-L-proline, dilithium salt A solution of the phenylmethyl ester product from part (b) (1.5 g., 2.6 mmole) and 10% palladium on carbon catalyst in ethanol (200 ml.) is hydrogenated on the Parr apparatus at 30 psi for 6.5 hours. The mixture is filtered, concentrated, taken up in ethanol and millipore filtered. The resulting solution is then concentrated, dissolved in 1N lithium hydroxide (6 ml.) and washed with ether. The aqueous layer is then applied to AG50WX2(Li+) ion exchange resin and eluted with water. The acidic (pH5) fractions are combined and concentrated to give a clear glass which is dissolved in water and lyoplilized to give 600 mg. of (trans)-1-[N-[(2-carboxycyclopentyl)carbonyl]-L-alanyl]-L-proline, dilithium salt as a white solid; m.p. (225) greater than 230°. TLC ($R_f$ 0.59 silica gel, n-butanol:acetic acid:ethyl acetate:water; 1:1:1:1). $[\alpha]_D = -105°$ (c=1.8, water).

Anal. Calc'd. for $C_{15}H_{20}N_2O_6Li_2 \cdot 0.5\ H_2O$: C, 50.39; H, 6.20; N, 7.83. Found: C, 50.39; H, 5.98; N, 7.83.

EXAMPLE 24

(cis)-1-[N-[(2-Carboxycyclohexyl)carbonyl]-L-alanyl]-L-proline (a)

(cis)-1-[N-[(2-Carboxycyclohexyl)carbonyl]-L-alanyl]-L-proline, 1,1-dimethylethyl ester To a solution of L-alanyl-L-proline, 1,1-dimethylethyl ester (1.03 g., 4.25 mmole) in methylene chloride (25 ml.) is added cis-1,2-cyclohexanedicarboxylic anhydride (650 mg., 4.25 mmole). The reaction mixture is stirred for 72 hours at 26° whereupon it is concentrated under reduced pressure and the residue partitioned between ethyl acetate and aqueous sodium bicarbonate solution. The aqueous layer is washed once more with ethyl acetate and then acidified to pH 3 with 10% potassium bisulfate and saturated with sodium chloride. Extraction with ethyl acetate (4 times) followed by drying (Na$_2$SO$_4$), and evaporation gives 1.05 g. of (cis)-1-[N-[(2-carboxycyclohexyl)carbonyl]-L-alanyl]-L-proline, 1,1-dimethylethyl ester as a white foam.

(b)

(cis)-1-[N-[[2-[(Diphenylmethoxy)carbonyl]cyclohexyl]carbonyl]-L-alanyl]-L-proline, 1,1-dimethylethyl ester To a solution of the 1,1-dimethylethyl ester product from part (a) (1.05 g., 2.65 mmole) in ethyl acetate (50 ml.) is added a solution of diphenyldiazomethane (0.781 g., 4.0 mmole) in ethyl acetate (10 ml.). The reaction mixture is stirred overnight at 26°, then evaporated and chromatographed to give 0.85 g. of (cis)-1-[N-[[2-[(diphenylmethoxy)carbonyl]cyclohexyl]carbonyl]-L-alanyl]-L-proline, 1,1-dimethylethyl ester as a white foam.

(c)

(cis)-1-[N-[(2-Carboxycyclohexyl)carbonyl]-L-alanyl]-L-proline

The ester product from part (b) (0.85 g., 1.51 mmole) is added to cold (0°) distilled trifluoroacetic acid (10 ml.) containing anisole (0.5 ml.). After 30 minutes at 0°, the volatiles are removed in vacuo, and the residue chased with toluene (two times). The residue is partitioned between ethyl acetate and aqueous sodium bicarbonate and the aqueous layer is washed again with ethyl acetate. The aqueous layer is acidified to pH 3 with 10% potassium bisulfate, saturated with sodium chloride, and extracted with ethyl acetate (three times). The combined ethyl acetate extracts are dried (Na$_2$SO$_4$), concentrated in vacuo, and the residue triturated with ether. White solids are collected by filtration to give 495 mg. of (cis)-1-[N-[(2-carboxycyclohexyl)carbonyl]-L-alanyl]-L-proline. TLC ($R_f$ 0.63 silica gel, n-butanol:acetic acid:water, 1:1:1:1; minor spot at $R_f$ 0.85).

Anal. Calc'd. for $C_{16}H_{24}N_2O_6 \cdot$ ethyl acetate: C, 54.00; H, 6.99; N, 6.99. Found: C, 53.25; H, 6.72; N, 6.93.

EXAMPLE 25

(trans)-1-[N-[(2-Carboxycyclohexyl)carbonyl]-L-alanyl]-L-proline (a)

(trans)-1-[N-[(2-Carboxycyclohexyl)carbonyl]-L-alanyl]-L-proline, phenylmethyl ester A mixture of trans-1,2-cyclohexanedicarboxylic anhydride (1.14 g., 7.5 mmole), L-alanyl-L-proline, phenylmethyl ester tosylate salt (3.54 g., 7.52 mmole), and diisopropylethylamine are stirred in tetrahydrofuran (75 ml.) overnight at 26°. Volatiles are removed in vacuo and the residue is dissolved in ethyl acetate and washed twice with water. The organic layer is extracted twice with sodium bicarbonate, and the combined aqueous extracts are adjusted to pH 3 with 10% potassium bisulfate. Extraction with ethyl acetate followed by drying (Na$_2$SO$_4$) and concentration under reduced pressure gives 2.5 g. of (trans)-1-[N-[(2-carboxycyclohexyl)carbonyl]-L-alanyl]-L-proline, phenylmethyl ester as a white foam.

(b)

(trans)-1-[N-[(2-Carboxycyclohexyl)carbonyl]-L-alanyl]-L-proline, bis(diphenylmethyl)ester A solution of the phenylmethyl ester product from part (a) (2.5 g., 5.82 mmole) in 95% ethanol (100 ml.) containing 10% palladium on carbon catalyst (2.5 g.) is hydrogenated overnight. After filtration, the catalyst is washed with 95% ethanol and the combined washings and filtrate are concentrated to a white foamy solid. Trituration with hexane gives 1.7 g. of crude white solid diacid product.

This impure diacid (1.68 g., 4.93 mmole) is dissolved in ethyl acetate (80 ml.) and treated with a solution of diphenyldiazomethane (2.10 g., 10.84 mmole) in ethyl acetate (10 ml.). After stirring overnight, the mixture is washed with sodium bicarbonate (two times) and brine (two times), and dried (Na$_2$SO$_4$). Concentration gives a purple oil which is chromatographed on silica gel to give 1.10 g. of (trans)-1-[N-[(2-carboxycyclohexyl)carbonyl]-L-alanyl]-L-proline, bis(diphenylmethyl)ester.

(c)

(trans)-1-[N-[(2-Carboxycyclohexyl)carbonyl]-L-alanyl]-L-proline

A cold (0°) solution of the diphenylmethyl ester product from part (b) (1.1 g., 1.63 mmole) in trifluoroacetic acid (10 ml.) containing anisole (0.5 ml.) is stirred for 30 minutes. The volatiles are removed in vacuo and the residue chased twice with toluene. The product is partitioned between saturated sodium bicarbonate and ethyl acetate and the aqueous layer is washed twice with ethyl acetate. The aqueous layer is adjusted to pH 3 with 10% potassium bisulfate, saturated with sodium chloride, and extracted with ethyl acetate (three times). The combined extracts are dried (Na$_2$SO$_4$) and concentrated to a white foam. Trituration with ether gives 456 mg. of (trans)-1-[N-[(2-carboxycyclohexyl)carbonyl]-L-alanyl]-L-proline as a white solid. TLC ($R_f$ 0.62, 0.58 (isomers) silica gel, n-butanol:acetic acid:water; 3:1:1).

Anal. Calc'd. for $C_{16}H_{24}N_2O_6 \cdot 0.75 H_2O$: C, 54.30; H, 6.83; N, 7.91. Found: C, 54.91; H, 6.47; N, 7.70.

EXAMPLE 26

(d-trans)-1-[N-[(2-Carboxycyclohexyl)carbonyl]-L-alanyl]-L-proline (a) (trans)-1,2-Cyclohexanedicarboxylic acid To a chilled solution of (trans)-1,2-cyclohexanedicarboxylic anhydride (87.5 g., 0.567 mole) in dioxane (300 ml.) is added dropwise over a 30 minute period 2N sodium hydroxide (567 ml., 1.134 mole). The reaction mixture is stirred for one hour (0° to room temperature), washed with ethyl acetate (3×600 ml.) and the aqueous layer is acidified with concentrated hydrochloric acid. The precipitated product is collected by filtration as white solids which are dried ($P_2O_5$) to give 104 g. of (trans)-1,2-cyclohexanedicarboxylic acid; m.p. 228°–231°.

(b) (d-trans)-1,2-Cyclohexadicarboxylic acid

To a filtered solution of (trans)-1,2-cyclohexanedicarboxylic acid (52 g., 0.302 mole) in n-propanol (1.85 l.) is added a solution of l(−)α-methyl benzyl amine (36.6 g., 0.302 mole) in n-propanol (0.11 l.). After standing for 2 days under refrigeration, the crude salt is collected as white solids (20.8 g.). This crude salt is twice recrystallized from n-propanol (195 ml., respectively) to afford 13.0 g. of pure salt as white solids. This pure salt is dissolved in 1N hydrochloric acid (150 ml.) and the solution is extracted with ether (5×200 ml.). The ether extracts are dried (MgSO$_4$) and concentrated on a rotary evaporator to give 5.2 g. of (d-trans)-1,2-cyclohexanedicarboxylic acid; $[\alpha]_D^{25} = +20.3°$ (c=1.5, acetone).

(c) (d-trans)-1,2-Cyclohexanedicarboxylic acid, mono(phenylmethyl)ester

To a cold suspension of (d-trans)-1,2-cyclohexadicarboxylic acid (3.87 g., 22.5 mmole) in ether (150 ml.) is added dropwise over a 10 minute period a solution of dicyclohexylcarbodiimide (4.64 g., 22.5 mmole) in ether (20 ml.). After stirring for 2.5 hours at 0°, the reaction mixture is filtered, and to the filtrate (0°) is added diisopropylethylamine (2.9 g., 3.92 ml., 22.5 mmole) and benzyl alcohol (4.86 g., 4.66 ml., 22.5 mmole). The reaction mixture is stirred overnight (0° to room temperature), filtered, and the filtrate is extracted with saturated sodium bicarbonate (2×50 ml.). The aqueous layer is acidified to a pH of 2 with 10% potassium bisulfate, saturated with sodium chloride, and extracted with ethyl acetate (4×100 ml.). The combined extracts are dried (Na$_2$SO$_4$) and concentrated to give 1.8 g. of (d-trans)-1,2-cyclohexanedicarboxylic acid, mono(phenylmethyl)ester as a colorless oil.

(d) (d-trans)-1-[N-[(2-Carboxycyclohexyl)carbonyl]-L-alanyl]-L-proline, bis(phenylmethyl)ester To a solution of (d-trans)-1,2-cyclohexanedicarboxylic acid, mono(phenylmethyl) ester (1.86 g., 6.86 mmole) in ether (25 ml.) is added dropwise oxalylchloride (0.96 g., 0.66 ml., 7.55 mmole) followed by a few drops of dimethylformamide. After stirring at room temperature for one hour, the solution is added to a cold (−10°) mixture of L-alanyl-L-proline, phenylmethyl ester tosylate salt ( 3.06 g., 6.86 mmole) and diisopropylethylamine (1.77 g., 2.38 ml., 13.72 mmole) in methylene chloride (45 ml.). After stirring overnight (−10° to room temperature), the reaction mixture is partitioned between ethyl acetate (100 ml.) and saturated aqueous sodium bicarbonate (100 ml.). The organic layer is washed with 1N hydrochloric acid (2×50 ml.), brine (2×50 ml.), dried (Na$_2$SO$_4$) and concentrated to a colorless oil. Chromatography on silica gel 60 (230–400 mesh) eluting with 15% ethyl acetate/methylene chloride gives 1.43 g. of (d-trans)-1-[N-[(2-carboxycyclohexyl)carbonyl]-L-alanyl]-L-proline, bis(phenylmethyl)ester as a colorless oil.

(e) (d-trans)-1-[N-[(2-Carboxycyclohexyl)carbonyl]-L-alanyl]-L-proline

A solution of the phenylmethyl ester product from part (d) (1.43 g., 2.75 mmole) in 95% ethanol (10 ml.) is added to a prehydrogenated suspension of palladium on carbon catalyst (200 mg.) in ethanol (90 ml.). This mixture is hydrogenated until the uptake is equal to 2 equivalents of hydrogen (123.2 ml., 5.5 mmole). The catalyst is filtered, washed with 95% ethanol and the filtrate and washings are concentrated under reduced pressure into a solid residue. Trituration with ether (3 times) affords 0.68 g. of (d-trans)-1-[N-[(2-carboxycyclohexyl) carbonyl]-L-alanyl]-L-proline as white solids; m.p. 72°–140° (slow decomposition). TLC (R$_f$0.54, 0.60 (minor) silica gel; n-butanol:acetic acid:water; 3:1:1). $[\alpha]_D = -82.8°$ (c=0.5, methanol).

Anal. Calc'd. for $C_{16}H_{24}N_2O_6 \cdot 0.3 H_2O$: C, 55,45; H, 7.18; N, 8.08. Found: C, 55.45; H, 7.05; N, 7.71.

EXAMPLE 27

(l-trans)-1-[N-[(2-Carboxycyclohexyl)carbonyl]-L-alanyl]-L-proline (a) (l-trans)-1,2-Cyclohexanedicarboxylic acid To a filtered solution of (trans)-1,2-cyclohexanedicarboxylic acid (52 g., 0.302 mole) [prepared as set forth in Example 26(a)] in n-propanol (1.85 l.) is added a solution of d(+)α-methyl benzyl amine (36.6 g., 0.302 mole) in n-propanol (0.11 l). After standing for 2 days under refrigeration, the crude salt is collected as white solids (22 g.). This crude salt is dissolved in 1N hydrochloric acid (300 ml.) and extracted into ether (5×300 ml.). The combined ether extracts are dried (MgSO$_4$) and concentrated on a rotary evaporator into 12.3 g. of white solids. In order to purify the compound, the free acid is reconverted into its salt and then liberated again to afford 10.1 g. of (l-trans)-1,2-cyclohexanedicarboxylic acid as white solids; $[\alpha]_D^{25} = -18.06°$ (c=1.5, acetone).

(b) (l-trans)-1-[N-[(2-Carboxycyclohexyl)carbonyl]-L-alanyl]-L-proline, phenylmethyl ester To a filtered, chilled (−5°) solution of (l-trans)-1,2-cyclohexanedicarboxylic acid (1.29 g., 7.5 mmole) in methylene chloride (110 ml., distilled) is added dicyclohexylcarbodiimide (1.54 g., 7.5 mmole) and a chilled (−5°) solution of L-alanyl-L-proline, phenylmethyl ester tosylate salt (3.88 g., 8.25 mmole) and diisopropylethylamine (1.06, 8.25 mmole). After 10 minutes of stirring heavy precipitation occurs. The reaction mixture is allowed to stir an additional 30 minutes (−5°), after which it is diluted with ethyl acetate (150 ml.) and extracted with saturated sodium bicarbonate (3×75 ml.). The combined aqueous extracts are acidified to a pH of 2 with 10% potassium bisulfate, saturated with sodium chloride and extracted with ethyl acetate (4×100 ml.). The combined ethyl acetate extracts are dried (Na$_2$SO$_4$) and concentrated in vacuo to give 1.4 g. of crude product. Flash chromatography on 140 g. of Merck Silica gel 60 (chloroform:methanol:formic acid; 70:10:1) affords 0.5 g. of pure (l-trans)-1-[N-[(2-carboxycyclohexyl)carbonyl]-L-alanyl]-L-proline, phenylmethyl ester as a colorless oil.

(c) (l-trans)-1-[N-[(2-Carboxycyclohexyl)carbonyl]-L-alanyl]-L-proline

A solution of the phenylmethyl ester product from part (b) (0.5 g., 1.16 mmole) in 95% ethanol (50 ml.) containing 10% palladium on carbon catalyst (200 mg.) is hydrogenated under atmospheric pressure overnight. The catalyst is filtered, washed with 95% ethanol and the washings and the filtrate are concentrated under reduced pressure to give 250 mg. of a white foam. Flash chromatography on 25 g. of Merck Silica gel 60 (chloroform:methanol:formic acid; 70:15:1) affords 210 mg. of pure (l-trans)-1-[N-[(2-carboxycyclohexyl)carbonyl]-L-alanyl]-L-proline as white solids; m.p. 76°-95° (slow decomposition). TLC (R$_f$ 0.53 silica gel, n-butanol:acetic acid: water; 3:1:1). $[\alpha]_D^{25}= -111.5°$ (c=0.4, methanol).

Anal. Calc'd. for C$_{16}$H$_{24}$N$_2$O$_6$: C, 56.45; H, 7.10; N, 8.23. Found: C, 56.31; H, 7.29; N, 7.92.

EXAMPLE 28

(cis)-1-[N-[(2-Carboxycycloheptyl)carbonyl]-L-alanyl]-L-proline, dilithium salt

(a) (cis)-1,2-Cycloheptanedicarboxylic acid 1-(1-Cyclopenten-1-yl)pyrrolidine and 2-butynedioic acid, dimethyl ester are reacted according to the procedure set forth in J. O. C., Vol. 28, p. 1464 (1963) to yield 3-(1-pyrrolidinyl)-2,7-cycloheptadiene-1,2-dicarboxylic acid, dimethyl ester.

This dimethyl ester is then hydrogenated using platinic oxide as the catalyst in the presence of glacial acetic acid as set forth in J. O. C., Vol. 28, p. 1464 (1963) to yield 2-cycloheptene-1,2-dicarboxylic acid.

Treatment of this acid with acetic anhydride according to the procedure set forth in Coll. Czech. Chem. Comm., Vol. 26, p 262 (1961) yields 1-cycloheptene-1,2-dicarboxylic anhydride.

Hydrogenation of this anhydride using platinic oxide in acetic anhydride according to the procedure set forth in Coll. Czech. Chem. Comm., Vol. 26, p. 262 (1961) yields (cis)-1,2-cycloheptanedicarboxylic anhydride. Treatment with water and recrystallization gives (cis)-1,2-cycloheptanedicarboxylic acid.

(b) (cis)-1,2-Cycloheptanedicarboxylic acid, mono(diphenylmethyl)ester

To a stirring solution of (cis)-1,2-cycloheptanedicarboxylic acid (1.0 g., 5.3 mmole) in ethyl acetate (25 ml.) is added a solution of diphenyldiazomethane (1.0 g., 5.3 mmole) in ethyl acetate (25 ml.). The resulting deep red solution is stirred at 25° for 18 hours, after which it is a pale yellow color. The solution is extracted with 10% aqueous sodium bicarbonate solution. The organic phase is dried and concentrated to give 1.7 g. of product. The aqueous phase is acidified with concentrated hydrochloric acid and extracted with ethyl acetate (3 times). The extracts are combined, dried (MgSO$_4$) and concentrated to give 0.3 g. of product as a pale yellow oil.

Both samples of product are combined and crystallized on standing to give 2.0 g. of (cis)-1,2-cycloheptanedicarboxylic acid, mono(diphenylmethyl)ester.

(c) (cis)-1-[N-[[2-[(Diphenylmethoxy)carbonyl]cycloheptyl]carbonyl]-L-alanyl]-L-proline, phenylmethyl ester To a stirring solution of (cis)-1,2-cycloheptanedicarboxylic acid, mono(diphenylmethyl)ester (2.0 g.) in dry tetrahydrofuran (100 ml.) are added L-alanyl-L-proline, phenylmethyl ester tosylate salt (2.5 g., 5.6 mmole), 1-hydroxybenzotriazole hydrate (0.75 g., 5.6 mmole), dicyclohexylcarbodiimide (1.2 g., 5.8 mmole) and diisopropylethylamine (1 ml., 5.7 mmole). The resulting solution is stirred at room temperature overnight, then filtered and concentrated. The residual oil is dissolved in ethyl acetate, washed sequentially with 1N hydrochloric acid and 10% sodium bicarbonate, dried and concentrated. The concentrate is dissolved in ether, filtered and concentrated to a pale yellow foam. The product is chromatographed on LP-1 eluting with ethyl acetate:hexane (1:1). Fractions containing the desired material (R$_f$ 0.68 silica gel, ethyl acetate) are combined and concentrated to give 1.9 g. of (cis)-1-[N-[[2-[(diphenylmethoxy)carbonyl]cycloheptyl]carbonyl]-L-alanyl]-L-proline, phenylmethyl ester as a clear oil.

(d) (cis)-1-[N-[(2-Carboxycycloheptyl)carbonyl]-L-alanyl]-L-proline, dilithium salt A solution of the phenylmethyl ester product from part (c) (1.9 g., 3.0 mmole) in ethanol (125 ml.) containing palladium on carbon catalyst is hydrogenated on the Parr apparatus at 30 psi for 19 hours. The resulting solution is filtered and concentrated. The residue is then dissolved in 1N lithium hydroxide (3 ml.) and washed with ether. The aqueous layer is applied to AG50WX-2(Li+) and eluted with water. Fractions are combined and concentrated. The resulting dilithium salt is chromatographed on HP-20 eluting with water. Fractions containing the desired product are combined, concentrated, dissolved in water, and lyophilized to give 160 mg. of (cis)-1-[N-[(2-carboxycycloheptyl)carbonyl]-L-alanyl]-L-proline, dilithium salt as a white powder; m.p. 220° (dec.). $[\alpha]_D = -91°$ (c=1.1, water). TLC (R$_f$ 0.75 silica gel, n-butanol:acetic acid: ethyl acetate:water; 1:1:1:1).

Anal. Calc'd. for C$_{17}$H$_{24}$N$_2$O$_6$Li$_2$. 2.5 H$_2$O: C, 49.64; H, 7.11; N, 6.81. Found: C, 49.50; H, 7.15; N, 6.72.

EXAMPLE 29

(1α,2β,5α)-1-[N-[(2-Carboxy-5-methoxycyclohexyl)carbonyl]-L-alanyl]-L-proline, dilithium salt

(a) (trans)-4-Cyclohexenyl-1,2-dicarboxylic acid

To a 1 l. 3-necked flask fitted with a gas inlet and mechanical stirrer is added benzene (350 ml.) and aluminum chloride (33 g.). To this diethyl fumarate (82 ml.) is added portionwise over a period of 5 minutes. The solution immediately turns yellow and warms up as the aluminum chloride dissolves. Stirring is continued for 30 minutes while the solution cools to room temperature. A steady stream of butadiene is then introduced and the flask is cooled intermittently with an ice bath over a 45 minute period. Addition continues for 24 hours. The reaction is quenched with cautious addition of 1N hydrochloric acid (150 ml.). The layers are separated and the organic layer is washed sequentially with 1N hydrochloric acid, water, and 10% sodium bicarbonate. The solution is then dried (MgSO₄) and concentrated. The product is vacuum distilled twice and the fractions containing the desired product are combined to give 103.6 g. of (trans)-4-cyclohexenyl-1,2-dicarboxylic acid, diethyl ester as a clear colorless liquid.

A solution of this diethyl ester (103.6 g., 0.46 mole) in ethanol (1 l.) and 2.5 N potassium hydroxide (403 ml.) is refluxed on a steam bath for 5 hours. The solution is then cooled, concentrated to one half its original volume and diluted with water to 1 l. The resulting solution is washed with ether, acidified with 1N hydrochloric acid and concentrated. The residue is triturated with acetone, filtered and recrystallized from water to give 57 g. of (trans)-4-cyclohexenyl-1,2-dicarboxylic acid as a white crystalline solid; m.p. 168°-170°.

(b)
(trans)-4-Bromo-5-hydroxy-1,2-cyclohexanedicarboxylic acid, δ-lactone (trans)-4-Cyclohexene-1,2-dicarboxylic acid (25 g., 0.15 mole) is suspended in methylene chloride (200 ml.) and bromine (7.5 ml., 0.15 mole) is added dropwise over 4 hours. When the addition is completed, the mixture is concentrated by rotary evaporation. The residue is dissolved in tetrahydrofuran (200 ml.) and triethylamine (50 ml.) is added. The mixture is heated at reflux for 3 hours, after which it is cooled, filtered, and concentrated. The residue is dissolved in ethyl acetate, washed with 1N hydrochloric acid, dried (MgSO₄) and concentrated. Recrystallization of the residue from ethyl acetate gives 16 g. of (trans)-4-bromo-5-hydroxy-1,2-cyclohexanedicarboxylic acid, δ-lactone.

(c)
(trans)-4-Bromo-5-hydroxy-1,2-cyclohexanedicarboxylic acid, δ-lactone, 1,1-dimethylethyl ester To a solution of (trans)-4-bromo-5-hydroxy-1,2-cyclohexanedicarboxylic acid, δ-lactone (16 g., 64 mmole) in ether (300 ml.) are added dicyclohexylcarbodiimide (14 g., 68 mmole), tert-butanol (5 g., 68 mmole) and dimethylaminopyridine (1 g., catalyst). The mixture is stirred at 25° for 18 hours, after which it is filtered, washed sequentially with 1N hydrochloric acid and 10% sodium bicarbonate solution, dried, and concentrated. The residue is flash chromatographed (LP-1 silica, methylene chloride:carbon tetrachloride 1:1) to give a colorless semi-solid (9.0 g.) which is crystallized from hexane/ether to give 8.2 g. of (trans)-4-bromo-5-hydroxy-1,2-cyclohexanedicarboxylic acid, δ-lactone, 1,1-dimethylethyl ester; m.p. 76°-77°.

(d) (trans)-5-Hydroxy-1,2-cyclohexanedicarboxylic acid, δ-lactone, 1,1-dimethylethyl ester A mixture of (trans)-4-bromo-5-hydroxy-1,2-cyclohexanedicarboxylic acid, δ-lactone, 1,1-dimethylethyl ester (8.2 g., 27 mmole), tri-n-butyl tin hydride (13 ml.) and toluene (500 ml.) is heated at reflux for 18 hours, after which it is concentrated by rotary evaporation to give a grayish liquid. Flash chromatography (LP-1 silica, carbon tetrachloride to methylene chloride to ethyl acetate gradient) gives the desired product as the major fraction ($R_f$ 0.25 silica gel, methylene chloride). The compound solidifies on standing and is recrystallized from ether to give 3.0 g. of (trans)-5-hydroxy-1,2-cyclohexanedicarboxylic acid, δ-lactone, 1,1-dimethylethyl ester.

(e) (1α,2β,4β)-4-Hydroxy-1,2-cyclohexanedicarboxylic acid, 1-(1,1-dimethylethyl)ester A mixture of (trans)-5-hydroxy-1,2-cyclohexanedicarboxylic acid, δ-lactone, 1,1-dimethyl ester (2.5 g., 11 mmole), tetrahydrofuran (5 ml.), and 1N aqueous lithium hydroxide (15 ml., 15 mmole) is stirred at 25° for 22 hours, after which it is diluted with water and washed with ether. The aqueous layer is acidified with hydrochloric acid and extracted with ether. The extract is dried and concentrated to give 2.3 g. of (1α,2β,4β)-4-hydroxy-1,2-cyclohexanedicarboxylic acid, 1-(1,1-dimethylethyl) ester as a white solid.

(f) (1α,2β,4β)-4-Methoxy-1,2-cyclohexanedicarboxylic acid, 1-(1,1-dimethylethyl)ester To a suspension of sodium hydride (600 mg. of 60% dispersion, 15 mmole) in tetrahydrofuran (50 ml.) is added (1α,2β,4β)-4-hydroxy-1,2-cyclohexanedicarboxylic acid, 1-(1,1-dimethylethyl) ester (1.3 g., 5.3 mmole). The mixture is heated at reflux for one hour, after which it is cooled to 0° and methyl iodide (3 ml.) added. The mixture is stirred for 18 hours as it warms to 25°, after which it is diluted with water and washed with ether. The aqueous layer is then acidified and extracted with ether (3 times). The extracts are dried and concentrated to give a crude product. This crude material is leeched with a minimum amount of chloroform and the resulting solution is reconcentrated to give 600 mg. of (1α,2β,4β)-4-methoxy-1,2-cyclohexanedicarboxylic acid, 1-(1,1-dimethylethyl)ester.

(g)
(1α,2β,5α)-1-[N-[(2-Carboxy-5-methoxycyclohexyl)-carbonyl]-L-alanyl]-L-proline, bis(1,1-dimethylethyl)ester A mixture of (1α,2β,4β)-4-methoxy-1,2-cyclohexanedicarboxylic acid, 1-(1,1-dimethylethyl ester) (600 mg., 2.3 mmole), L-alanyl-L-proline, 1,1-dimethylethyl ester (600 mg., 2.3 mmole), dicyclohexylcarbodiimide (500 mg., 2.4 mmole), and 1-hydroxybenzotriazole hydrate (310 mg., 2.3 mmole) in tetrahydrofuran (25 ml.) is stirred at 25° for 20 hours, after which it is diluted with ether and filtered. The filtrate is washed sequentially with 1N hydrochloric acid and 10% aqueous sodium bicarbonate, dried, and concentrated. The residue is dissolve in ether, filtered, and reconcentrated to give a gummy oil. Filtration through a short column of Florisil (eluting first with chloroform to remove non-polar impurities, then with ethyl acetate) gives 600 mg. of (1α,2β,5α)-1-[N-[(2-carboxy-5-methoxycyclohexyl)carbonyl]-L-alanyl]-L-proline, bis(1,1-dimethylethyl)ester.

(h)
(1α,2β,5α)-1-[N-[(2-Carboxy-5-methoxycyclohexyl)-carbonyl]-L-alanyl]-L-proline, dilithium salt A solution of the ester product from part (g) (600 mg., 1.2 mmole) in trifluoroacetic acid (10 ml.) is stirred at 25° for 1.5 hours, after which it is concentrated by rotary evaporation. Toluene is then added to the residue and it is reconcentrated. The residue is then dissolved in 1N lithium hydroxide (1.2 ml.) and the solution is applied to a column of excess AG50WX2(Li+) and eluted with water. Concentration gives an off-white solid which is chromatographed on HP-20 (eluting with water). This material is combined with a sample from a previous, identical run [employing 250 mg. of the ester product from part (g)] and chromatographed again HP-20 and lyophilized to give 180 mg. of (1α,2β,5α)-1-[N-[(2-carboxy-5-methoxycyclohexyl)carbonyl]-L-alanyl]-L-proline, dilithium salt as a white solid; m.p. greater than 230°. TLC ($R_f$ 0.33 silica gel, ethyl acetate:pyridine:acetic acid: water; 45:20:6:11). $[\alpha]_D^{20} = -86°$ (c=2, water).

Anal. Calc'd. for $C_{17}H_{24}N_2O_7Li_2 \cdot 2H_2O$: C, 48.72; H, 6.73; N, 6.67. Found: C, 48.72; H, 6.83; N. 6.51.

EXAMPLE 30

(cis)-1-[N-[(6-Carboxy-3-cyclohexen-1-yl)carbonyl]-L-alanyl]-L-proline

(a)

(cis)-1-[N-[(6-Carboxy-3-cyclohexen-1-yl)carbonyl]-L-alanyl]-L-proline, bis(phenylmethyl) ester A solution of (cis)-4-cyclohexene-1,2-dicarboxylic acid, mono(phenylmethyl)ester (3 g., 11.5 mmole) [prepared by treating (cis)-4-cyclohexene-1,2-dicarboxylic anhydride with one equivalent each of benzyl alcohol and triethylamine] in 15 ml. of thionyl chloride is heated at 50° for 4 hours, after which the excess thionyl chloride is evaporated. To a portion of the acid chloride (1.5 g., 1.1 equivalent) in tetrahydrofuran is added L-alanine-L-proline, phenylmethyl ester tosylate salt (2.2 g., 4.89 mmole) and triethylamine (1.6 ml., 2.1 equivalent). The reaction mixture is stirred at ambient temperature overnight. The reaction mixture is then concentrated and the residue is dissolved in ethyl acetate. The ethyl acetate solution is washed sequentially with water, 10% sodium bicarbonate, 10% hydrochloric acid, water, and brine. After drying ($MgSO_4$), the solvent is evaporated leaving an oil which is purified by flash chromatography (LPS-2, methylene chloride:ethyl acetate, 4:1). The fractions containing the pure product are combined and concentrated to give 1.2 g. of (cis)-1-[N-[(6-carboxy-3-cyclohexen-1-yl)carbonyl]-L-alanyl]-L-proline, bis(phenylmethyl)ester as a colorless oil.

(b)

(cis)-1-[N-[(6-Carboxy-3-cyclohexen-1-yl)carbonyl]-L-alanyl]-L-proline

The phenylmethyl ester product from part (a) (1.2 g., 2.31 mmole) is dissolved in a solution of 10% sodium hydroxide (5 ml.) and methanol(5 ml.) and stirred at room temperature for 3 hours. The reaction mixture is diluted with water and washed with diethyl ether. Upon acidification of the aqueous layer with potassium bisulfate and saturation with sodium chloride, the diacid product is extracted into ethyl acetate and dried ($MgSO_4$). The ethyl acetate solution is concentrated and the residue is triturated with hexane and diethyl ether to give 400 mg. of 1-[N-[(6-carboxy-3-cyclohexen-1-yl)carbonyl]-L-alanyl]-L-proline as a white solid; m.p. softens at 98°, 125°-130°. TLC ($R_f$ 0.44 silica gel, methylene chloride:methanol:acetic acid; 8:1:1). $[\alpha]_D = -76.7°$ (c=1.4, methanol).

Anal Calc'd. for $C_{16}H_{22}N_2O_6$: C, 53.92; H, 6.79; N, 7.86. Found: C, 54.28; H, 6.59; N, 7.67.

EXAMPLE 31

(trans)-1-[N-[(6-Carboxy-3-cyclohexen-1-yl)carbonyl]-L-alanyl]-L-proline, dilithium salt

(a) (trans)-4-Cyclohexene-1,2-dicarboxylic anhydride

A solution of (trans)-4-cyclohexene-1,2-dicarboxylic acid (5 g., 2.9 mmole) [prepared as set forth in Example 29 (a)] in acetic anhydride (40 ml.) is heated on a steam bath for one hour. The solution is then cooled and concentrated to a white solid. Recrystallization from ethyl acetate gives 2.7 g. of (trans)-4-cyclohexene-1,2-dicarboxylic anhydride as a white crystalline solid; m.p. 174°-177°.

(b) (trans)-4-Cyclohexene-1,2-dicarboxylic acid, mono(phenylmethyl) ester

A solution of (trans)-4-cyclohexene-1,2-dicarboxylic anhydride (1.0 g., 6.6 mmole) and diisopropylethylamine (1 ml.) in benzyl alcohol (25 ml.) is stirred at room temperature for 18 hours. The resulting solution is diluted with 10% sodium bicarbonate and washed with ethyl acetate. The aqueous layer is then acidified with concentrated hydrochloric acid and extracted with ethyl acetate. The combined extracts are dried and concentrated to give 1.0 g. of (trans)-4-cyclohexene-1,2-dicarboxylic acid, mono(phenylmethyl) ester as a clear oil.

(c) (trans)-1-[N-[(6-Carboxy-3-cyclohexen-1-yl)carbonyl]-L-alanyl]-L-proline, bis(phenylmethyl) ester To a stirring solution of (trans)-4-cyclohexene-1,2-dicarboxylic acid, mono(phenylmethyl) ester (2.0 g., 7.7 mmole) in tetrahydrofuran (125 ml.) is added L-alanyl-L-proline, phenylmethyl ester tosylate salt (3.45 g., 7.7 mmole), 1-hydroxybenzotriazole hydrate (1.0 g., 7.7 mmole), dicyclohexylcarbodiimide (1.6 g., 7.7 mmole) and diisopropylethylamine (1.3 ml., 7.7 mmole). The resulting solution is stirred at room temperature for 22 hours. The mixture is then filtered, concentrated, dissolved in ethyl acetate, and washed sequentially with 1N hydrochloric acid and 10% sodium bicarbonate solution. The organic layer is dried ($MgSO_4$) and concentrated. The residue is dissolved in ether, millipore filtered and concentrated. The product is applied to LP-1 and eluted with hexane:ethyl acetate (1:1). Fractions containing the desired product ($R_f$ 0.6 silica gel, ethyl acetate) are combined and concentrated to give 2.85 g. of (trans)-1-[N-[(6-carboxy-3-cyclohexen-1-yl)carbonyl]-L-alanyl] -L-proline, bis(phenylmethyl)ester as a clear oil.

(d) (trans)-1-[N-[(6-Carboxy-3-cyclohexen-1-yl)carbonyl]-L-alanyl]-L-proline, dilithium salt A solution of the phenylmethyl ester product from part (c) (1.6 g., 3.1 mmole) in ethanol (7 ml.) and 1N lithium hydroxide (7 ml.) is stirred at room temperature for 16 hours. The resulting solution is diluted with water and washed with ether. The aqueous layer is then applied to AG50WX2(H+) and eluted with water. Fractions having acid to neutral pH are combined and concentrated. This material is then chromatographed on HP-20 using a water to ethanol gradient. Those fractions containing the desired material are combined and concentrated. The diacid product is then dissolved in water and applied to AG50WX2(Li+), eluting with water. Fractions containing the desired salt are then concentrated to give a clear glass which is then dissolved in water and lyophilized to give 700 mg. of (trans)-1-[N-[(6-carboxy-3-cyclohexen-1-yl)carbonyl]-L-alanyl]-L-proline, dilithium salt as a white powder; m.p. 175°-179° (dec.). TLC ($R_f$ 0.68 silica gel, n-butanol:acetic acid:water:ethyl acetate; 1:1:1:1). $[\alpha]_D = -79.7°$ (c=1.3, water).

Anal Calc'd. for $C_{16}H_{20}N_2O_6Li_2 \cdot 0.9 H_2O$: C, 52.43; H, 6.00; N, 7.64. Found: C, 52.35; H, 6.31; N, 7.75.

EXAMPLE 32

(trans)-1-[N-[(3-Carboxy-1,2,3,4-tetrahydro-2-naphthalenyl)carbonyl]-L-alanyl]-L-proline, dilithium salt

(a)
(trans)-1,2,3,4-Tetrahydro-2,3-naphthalenedicarboxylic acid, diethyl ester A solution of 1,2-bis(bromoethyl)benzene (26.4 g., 0.1 mole) in dimethyl formamide is added to a mixture of zinc dust (6.5 g., 0.1 g. atom), diethylfumarate (50 ml., 0.3 mole), and dimethylformamide (500 ml.) at 25° over 1 hour. When the addition is complete, the mixture is warmed to 50° and is stirred at that temperature for 3 hours, during which additional zinc dust (5 g.) is added in small portions. The mixture is then allowed to cool to 25° and is stirred for 18 hours. The resulting mixture is filtered and poured into 1N hydrochloric acid (1 l.). The solution is extracted with ether (4 times) and the extracts are washed with brine, dried, and concentrated. The residue is fractionally distilled (1 torr) to give a forerun of diethylfumarate (b.p. 75°) and then 8 g. of (trans)-1,2,3,4-tetrahydro-2,3-naphthalenedicarboxylic acid, diethyl ester; b.p. 170°.

(b)
(trans)-1,2,3,4-Tetrahydro-2,3-naphthalenedicarboxylic acid

A mixture of the ethyl ester product from part (a) (8 g., 29 mmole), ethanol (50 ml.), and 1N aqueous sodium hydroxide solution (100 ml.) is stirred at 25° for 16 hours, after which it is washed with ether and ethyl acetate. The aqueous phase is acidified with hydrochloric acid and extracted with ethyl acetate. The extract is dried and concentrated. The residue is triturated with ether to give 2.8 g. of (trans)-1,2,3,4-tetrahydro-2,3-naphthalenedicarboxylic acid as a white solid; m.p. 229°–232°.

(c)
(trans)-1,2,3,4-Tetrahydro-2,3-naphthalenedicarboxylic anhydride

The acid product from part (b) (1.4 g., 4.5 mmole) in acetyl chloride (20 ml.) is heated at reflux for 3 hours, after which it is cooled in an ice bath. The solid precipitate which forms is collected and recrystallized from 1:1 ethyl acetate:benzene to give 1.0 g. of (trans)-1, 2,3,4-tetrahydro-2,3-naphthalenedicarboxylic anhydride; m.p. 233°–234°.

(d)
(trans)-1,2,3,4-Tetrahydro-2,3-naphthalenedicarboxylic acid, mono(phenylmethyl)ester Sodium metal (about 50 mg.) is dissolved in benzyl alcohol (30 ml.). The anhydride product from part (c) (800 mg., 3.96 mmole) is then added and the mixture is stirred at 25° for 21 hours. The mixture is then diluted with a large volume of ether and the white precipitate which forms is collected and recrystallized from methnaol/ether to give 300 mg. of (trans)-1,2,3,4-tetrahydro-2,3-naphthalenedicarboxylic acid, mono(phenylmethyl) ester.

(e)
(trans)-1-[N-[(3-Carboxy-1,2,3,4-tetrahydro-2-naphthalenyl)carbonyl]-L-alanyl]-L-proline, bis(phenylmethyl)ester A mixture of the phenylmethyl ester product from part (d) (330 mg., 1 mmole), L-alanyl-L-proline, phenylmethyl ester tosylate salt (500 mg., 1.1 mmole), diisopropylethylamine (200 μl., 1.1 mmole), dicyclohexylcarbodiimide (230 mg., 1.1 mmole), and 1-hydroxybenzotriazole hydrate (150 mg., 1.1 mmole) in tetrahydrofuran (10 ml.) is stirred at 25° for 40 hours, after which it is concentrated by rotary evaporation. The residue is dissolved in ethyl acetate and filtered. The filtrate is washed sequentially with 1N hydrochloric acid and 10% aqueous sodium bicarbonate, dried, and concentrated. The residue is dissolved in ether, filtered, and reconcentrated to give 650 mg. of (trans)-1-[N-[(3-carboxy-1,2,3,4-tetrahydro-2-naphthalenyl)carbonyl]-L-alanyl]-L-proline, bis(phenylmethyl)ester.

(f)
(trans)-1-[N-[(3-Carboxy-1,2,3,4-tetrahydro-2-naphthalenyl)carbonyl]-L-alanyl]-L-proline, dilithium salt A solution of the phenylmethyl ester product from part (e) (650 mg., 1.14 mmole) and 10% palladium on carbon catalyst (50 mg.) in 1:1:1 ethyl acetate:ethanol:water (150 ml.) is hydrogenated on a Parr apparatus at 25 psi for 17 hours, after which it is filtered and concentrated. The residue is dissolved in water containing about 1-molar equivalent of lithium hydroxide. The aqueous solution is washed with ether and then passed through a column of excess AG50(Li+) resin. The eluant is concentrated and chromatographed on HP-20 (eluting with water) to give the salt product as a white solid. This material is dissolved in water and lyophilized to give 100 mg. of (trans)-1-[N-[(3-carboxy-1,2, 3,4-tetrahydro-2-naphthalenyl)carbonyl]-L-alanyl]-L-proline, dilithium salt as a free flowing white powder; m.p. greater than 230°. TLC ($R_f$ 0.35 silica gel; ethyl acetate:pyridine:acetic acid: water; 45:20:6:11). $[\alpha]_D^{20} = -90°$ (c=0.5, 1N hydrochloric acid).

Anal. Calc'd for $C_{20}H_{22}N_2O_6Li_2 \cdot 2H_2O$: C, 55.05; H, 6.01; N, 6.42. Found: C, 54.85; H, 5.87; N, 6.58.

EXAMPLE 33

(S)-2-[2-[[[(trans)-2-Carboxycyclohexyl]carbonyl]amino]-1-oxopropyl]-1,2,3,4-tetrahydro-3-isoquinolinecarboxylic acid

(a)
(S)-2-[N-[(1,1-Dimethylethoxy)carbonyl]-L-alanyl]-1,2,3,4-tetrahydro-3-isoquinolinecarboxylic acid,phenylmethyl ester A mixture of N-[(1,1-dimethylethoxy)carbonyl]-L-alanine (4.7 g., 25 mmole), (S)-1,2,3,4-tetrahydro-3-isoquinolinecarboxylic acid, phenylmethyl ester tosylate salt (10.98 g., 25 mmole), dicyclohexylcarbodiimide (5.15 g., 25 mmole), 1-hydroxybenzotriazole hydrate (3.82 g., 25 mmole) and diisopropylethylamine (3.23 g., 4.36 ml., 25 mmole) in tetrahydrofuran (300 ml., distilled) is stirred overnight at room temperature. The precipitated urea is filtered and the filtrate is concentrated to an oil. The residue is redissolved in ethyl acetate (200 ml.), washed with saturated aqueous sodium bicarbonate (2×100 ml.), 10% potassium bisulfate (2×100 ml.), and water (2×100 ml.), then dried ($Na_2SO_4$) and concentrated under reduced pressure to give 9.1 g. of (S)-2-[N-[(1,1-dimethylethoxy)carbonyl]-L-alanyl]-1,2,3,4-tetrahydro-3-isoquinolinecarboxylic acid, phenylmethyl ester as an oil.

(b)
(S)-2-(L-Alanyl)-1,2,3,4-tetrahydro-3-isoquinolinecarboxylic acid, phenylmethyl ester, tosylate salt.

A cold (0°) solution of the phenylmethyl ester product from part (a) (9.1 g., 20.7 mmole) in trifluoroacetic acid (25 ml.) is stirred for 15 minutes. The volatiles are removed in vacuo and the residue chased with toluene (two times). The oily residue is redissolved in ether (100 ml.) and treated with a solution of p-toluenesulfonic acid monohydrate (4.3 g., 22.7 mmole) in warm ether (200 ml.). The precipitated product is collected by filtration to give 8.6 g. of white solids. Recrystallization from warm methanol (15 ml.)/ether gives 7.1 g. of pure (S)-2-(L-alanyl)-1,2,3,4-tetrahydro-3-isoquinolinecarboxylic acid, phenylmethyl ester, tosylate salt as a white solid.

(c) (trans)-1,2-Cyclohexanedicarboxylic acid, mono(phenylmethyl)ester

A mixture of (trans)-1,2-cyclohexanedicarboxylic anhydride (10.02 g., 65 mmole), benzyl alcohol (7.03 g., 6.72 ml., 65 mmole), diisopropylethylamine (8.40 g., 11.32 ml., 65 mmole) and a catalytic amount of dimethylaminopyridine are stirred in methylene chloride (100 ml.) overnight. Volatiles are removed in vacuo and the residue is portioned between saturated aqueous sodium bicarbonate (100 ml.) and ethyl acetate (100 ml.). The aqueous layer is washed twice with ethyl acetate, acidified to a pH of 2 by the addition of 10% potassium bisulfate, saturated with sodium chloride and extracted with ethyl acetate (3×75 ml.). The combined extracts are dried ($Na_2SO_4$) and concentrated to give 12.8 g. of (trans)-1,2-cyclohexanedicarboxylic acid, mono(phenylmethyl) ester as an oil.

(d)
(S)-2-[2-[[[(trans)-2-Carboxylcyclohexyl]-carbonyl]amino]-1-oxopropyl]-1,2,3,4-tetrahydro-3-isoquinolinecarboxylic acid, bis (phenylmethyl)ester To a solution of (trans)-1,2-cyclohexanedicarboxylic acid, mono(phenylmethyl) ester (810 mg., 3.1 mmole) in ether (10 ml.) is added dropwise oxalyl chloride (430 mg., 0.297 ml., 3.41 mmole) followed by a few drops of dimethylformamide. After stirring for 1 hour at 25°, the solution is added to a cold (-10°) mixture of (S)-2-(L-alanyl)-1,2,3,4-tetrahydro-3-isoquinolinecarboxylic acid, phenylmethyl ester, tosylate salt (1.57 g., 3.1 mmole) and diisopropylethylamine (790 mg., 1.07 ml., 6.2 mmole) in methylene chloride (20 ml.). After stirring overnight (−10°→room temperature), the reaction mixture is portioned between ethyl acetate (100 ml.) and saturated aqueous sodium bicarbonate (100 ml.). The organic layer is washed with 1N hydrochloric acid (2×50 ml.), brine (2×50 ml.), dried ($Na_2SO_4$) and concentrated to a yellow oil (800 mg.). Chromatography (PLC, silica gel, 20% methanol/chloroform) gives 470 mg. of (S)-2-[2-[[[(trans)-2-carboxycyclohexyl]carbonyl]amino]-1-oxopropyl]-1,2,3,4-tetrahydro-3-isoquinolinecarboxylic acid, bis(phenylmethyl)ester as a pale yellow solid.

(e)
(S)-2-[2-[[[(trans)-2-Carboxycyclohexyl]carbonyl]amino]-1-oxopropyl]-1,2,3,4-tetrahydro-3-isoquinolinecarboxylic acid A solution of the phenylmethyl ester product from part (d) (450 mg., 0.77 mmole) in 95% ethanol (25 ml.) containing 10% palladium on carbon catalyst (200 mg.) is hydrogenated under atmospheric pressure overnight. The catalyst is removed by filtration and washed thoroughly with ethanol. The combined filtrate and washings are concentrated under reduced pressure to a white foam which is triturated twice with ether to give 170 mg. of (S)-2-[2-[[[(trans)-2-carboxycyclohexyl]carbonyl]amino]-1-oxopropyl]-1,2,3,4-tetrahydro-3-isoquinolinecarboxylic acid as white solids. TLC ($R_f$ 0.72 silica gel; n-butanol:acetic acid:water, 3:1:1).

Anal. Calc'd. for $C_{21}H_{26}N_2O_6 \cdot 1.3\ H_2O$: C, 59.22; H, 6.76; N, 6.57. Found: C, 59.23; H, 6.59; N, 6.32.

EXAMPLE 34

N-[N-(3-Carboxy-1-oxopropyl)-L-phenylalanyl]-L-leucine (a) L-Phenylalanyl-L-leucine, 1,1-dimethylethyl ester, p-toluenesulfonic acid salt p-Toluenesulfonic acid (8.12 g., 42.7 mmole) is added to an ice-chilled solution of N-[N-[(phenylmethoxy)carbonyl]-L-phenylalanyl]-L-leucine, 1,1-dimethylethyl ester (20 g., 42.68 mmole) in 95% ethanol (325 ml.). The reaction vessel is purged with argon, and 10% palladium on carbon catalyst (2.0 g.) is added. The mixture is placed under 1 atmosphere of hydrogen and stirred for 20 hours. Filtering off the catalyst and concentrating the filtrate produces a sticky white solid which is triturated with ethyl ether and dried in vacuo to give 18.75 g. of L-phenylalanyl-L-leucine, 1,1-dimethylethyl ester, p-toluenesulfonic acid salt; m.p. (softens at 145°) 157°–159.5°.

(b)
N-[N-(3-Carboxy-1-oxopropyl)-L-phenylalanyl]-L-leucine, 1,1-dimethylethyl ester A stirred solution of L-phenylalanyl-L-leucine, 1,1-dimethylethyl ester, p-toluenesulfonic acid salt (2.53 g., 4.99 mmole) and succinic anhydride (0.5 g., 5.0 mmole) in tetrahydrofuran (60 ml.) is purged with nitrogen. Diisopropylethylamine (0.87 ml., 5.0 mmole) is added in one portion with vigorous stirring, and the mixture is allowed to react overnight at room temperature. The solvent is removed in vacuo, and the clear, light yellow residue is taken up in ethyl acetate. The solution is washed with 10% potassium bisulfate (30 ml.), brine (30 ml.), and saturated sodium bicarbonate (30 ml.). Upon washing with sodium bicarbonate, a third layer is formed between the organic and aqueous layers. This third layer does not decrease visibly in volume on repeated washings with sodium bicarbonate. It is separated out and treated with ethanol whereupon a white solid forms which is removed by suction filtration. The filtrate is dried ($MgSO_4$) and concentrated in vacuo to give 1.58 g. of N-[N-(3-carboxy-1-oxopropyl)-L-phenylalanyl]-L-leucine, 1,1-dimethylethyl ester as a white solid; m.p. 156°–162° with decarboxylation.

(c)
N-[N-(3-Carboxy-1-oxopropyl)-L-phenylalanyl]-L-leucine

To a solution of the ester product from part (b) (1.34 g., 3.08 mmole) in acidic acid (6.8 ml.) is added approximately 1.5 M hydrochloric acid (20.5 ml.), prechilled to approximately 10°. The resulting light yellow solution is stirred for one hour, while warming to room temperature, and then concentrated in vacuo. Benzene is added and the mixture is again concentrated to remove residual acetic acid (twice), and the residue is dried in vacuo to a white solid. This material is recrystallized from ethyl acetate/hexane to a gummy material which is triturated in the mother liquor to a white solid (0.61 g.). Upon standing, an additional 0.11 g. of product crystallizes from the mother liquor. These solids are combined to give a total of 0.72 g. of N-[N-(3-carboxy-1-oxopropyl)-L-phenylalanyl]-L-leucine; m.p. 156.5°–158°. TLC ($R_f$=0.24 silica gel; benzene:acetic acid, 4:1); $[\alpha]_D^{25}$=−20.2°0 (c=1, methanol).

Anal. Calc'd. for $C_{19}H_{26}N_2O_6 \cdot 0.2\ H_2O$: C, 59.74; H, 6.97; N, 7.33. Found: C, 59.86; H, 7.00; N, 7.11.

EXAMPLE 35

(trans)-N-[N-[(2-Carboxycyclohexyl)carbonyl]-L-phenylalanyl]-L-leucine

(a) (trans)-1,2-Cyclohexanedicarboxylic acid, mono(phenylmethyl)ester

To a solution of (trans)-1,2-cyclohexanedicarboxylic anhydride (3.08 g., 20 mmole) in benzyl alcohol (10 ml.) is added diisopropylethylamine (1.2 ml., 6.9 mmole) in one portion. The solution is stirred overnight at room temperature under a drying tube, then poured into saturated sodium bicarbonate (100 ml.) and extracted with ethyl acetate (3×30 ml.). The organic layers are collected, washed with water and brine (30 ml. each), dried ($Na_2SO_4$), and concentrated in vacuo to give 13.8 g. of (trans)-1,2-cyclohexanedicarboxylic acid, mono(phenylmethyl) ester as a clear, colorless oil which partially crystallizes on standing.

(b) L-Phenylalanyl-L-leucine, phenylmethyl ester, hydrochloride

N-[(1,1-Dimethylethoxy)carbonyl]-L-phenylalanine (21.22 g., 80 mmole), L-leucine, phenylmethyl ester, tosylate salt (31.48 g., 80 mmole), 1-hydroxybenzotriazole hydrate (10.81 g., 80 mmole), and diisopropylethylamine (13.94 ml., 80 mmole) are suspended in tetrahydrofuran (400 ml.) and chilled to −5° with mechanical stirring. A solution of dicyclohexylcarbodiimide (16.51 g., 80 mmole) in tetrahydrofuran (40 ml.) is added over 15 minutes under a drying tube. The mixture is stirred overnight, warming to room temperature. The dicyclohexylurea is filtered (washed-ethyl acetate 2x) and the filtrate concentrated to a yellow solid. This material is taken up in ethyl acetate (30 ml.), filtered, and the filtrate washed sequentially with 10% potassium bisulfate, 50% brine, saturated sodium bicarbonate, 50% brine, and brine (100 ml. each)(repeatedly forms emulsions, filtered several times). It is then dried ($Na_2SO_4$) and concentrated in vacuo to give 35.68 g. of N-[N-[(1,1-dimethylethoxy)carbonyl]-L-phenylalanyl]-L-leucine, phenylmethyl ester as a white solid.

A portion of N-[N-[(1,1-dimethylethoxy)carbonyl]-L-phenylalanyl]-L-leucine, phenylmethyl ester (21.09 g., 45 mmole) is mixed with prechilled (−10°) trifluoroacetic acid (70 ml.) containing anisole (1.8 ml.), flushed with nitrogen, and allowed to react for 3 hours in the cold. The dark orange reaction mixture is then concentrated in vacuo, chased with toluene (40 ml.), and poured into ethyl ether (600 ml.). The resulting white precipitate is filtered, washed with ethyl ether (3×80 ml.), and dried in vacuo to give 17.98 g. of L-phenylalanyl-L-leucine, phenylmethyl ester, trifluoroacetic acid salt as a white solid; m.p. 149.5°–151°.

A portion of L-phenylalanyl-L-leucine, phenylmethyl ester, trifluoroacetic acid salt (13.00 g., 25.17 mmole) is slurried in ethyl acetate (50 ml.) and to it, with vigorous stirring, is added a prechilled solution of dry hydrochloric acid (approximately 7.5 g.) in ethyl acetate (150 ml.). The mixture is allowed to react for 30 minutes at room temperature, and the resulting precipitate is thoroughly triturated. The mixture is warmed to 35° (steam cone), triturated again, and filtered to yield a white solid. The addition of pentane (250 ml.) to the filtrate produces additional white, needle-like, crystalline solids. These solids are pooled and dried ($P_2O_5$) overnight to yield 10.11 g. of L-phenylalanyl-L-leucine, phenylmethyl ester, hydrochloride; m.p. 160°–161.5°.

(c) (trans)-N-[N-[(2-Carboxycyclohexyl)carbonyl]-L-phenylalanyl]-L-leucine, bis(phenylmethyl)ester A solution of (trans)-1,2-cyclohexanedicarboxylic acid, mono(phenylmethyl)ester (1.31 g., 5.00 mmole), L-phenylalanyl-L-leucine, phenylmethyl ester, hydrochloride (2.02 g., 5.00 mmole), 1-hydroxybenzotriazole hydrate (0.68 g., 5.0 mmole) and diisopropylethylamine (0.87 ml., 5.0 mmole) in tetrahydrofuran (50 ml.) is chilled, under a drying tube, to −5°. Dicyclohexycarbodiimide (1.03 g., 5.00 mmole) in tetrahydrofuran (10 ml.) is added while maintaining the reaction temperature below 0°. The mixture is stirred overnight, warming to room temperature, filtered, and the solvent removed in vacuo. The white solid residue is taken up in ethyl acetate (60 ml.) (gentle warming), again filtered, then washed with 10% potassium bisulfate, and concentrated in vacuo to a gummy, semicrystalline material (2.92 g.). Most of this material (2.78 g.) is applied to column of silica gel LPS-1 (200 g.) and eluted with 5.3:1 hexane/acetone. After a void volume of 300 ml., fractions of 50ml. each are collected and fraction numbers 22–27 are pooled and concentrated to give 1.72 g. of (trans)-N-[N-[(2-carboxycyclohexyl) carbonyl]-L-phenylalanyl]-L-leucine, bis(phenylmethyl) ester as a white solid.

(d) (trans)-N-[N-[(2-Carboxycyclohexyl)carbonyl]-L-phenylalanyl]-L-leucine

A solution of the bis(phenylmethyl)ester product from part (c)(10.90 g., 1.5 mmole) in 95% ethanol (60 ml.) is flushed with argon and 10% palladium on carbon catalyst (0.09 g.) is added. The mixture is placed under one atmosphere of hydrogen and stirred overnight. It is then filtered and concentrated in vacuo to a gummy light oil (0.64 g.). This material is applied to a column of silica gel (230–400 mesh, 35 g.) and eluted with 5:1 toluene/acetic acid. After a void volume of 150 ml., 21 ml. fractions are collected. Fractions numbered 7–11 are pooled and concentrated in vacuo (add benzene and again concentrate to azeotropically remove residual acetic acid) to give 0.35 g. of (trans)-N-[N-[(2-carboxycyclohexyl)carbonyl]-L-phenylalanyl]-L-leucine as an amorphous white solid; m.p. 132°–181°. TLC (silica gel $R_f$=0.18, 0.22; 5:1 toluene/acetic acid).

Anal. Calc'd. for $C_{23}H_{32}N_2O_6$: C, 63.87; H, 7.45; N, 6.47. Found: C, 63.69; H, 7.39; N, 6.27.

EXAMPLE 36

(cis)-N-[N-[(2-Carboxycyclohexyl)carbonyl]-L-phenylalanyl]-L-proline (a) (cis)-1,2-Cyclohexanedicarboxylic acid, mono(phenylmethyl)ester To a solution of (cis)-1,2-cyclohexanedicarboxylic anhydride (3.08 g., 20 mmole) in benzyl alcohol (6 ml.) under nitrogen is added, in one portion, diisopropylethylamine (1.2 ml., 6.9 mmole). The ensuing reaction is quite exothermic (pot temperature greater than 60° at 5 minutes). The mixture is cooled in a room temperature water bath overnight. The resulting light yellow solution is poured into saturated sodium bicarbonate (100 ml.) and extracted with ethyl acetate (3×30 ml.). The aqueous portion is acidified to a pH of approximately 1.5 with concentrated hydrochloric acid, then extracted again with ethyl acetate (3×30 ml.). The organic layers are combined, washed with 0.1 N hydrochloric acid, 50% brine, and brine (30 ml. each), dried ($Na_2SO_4$, and concentrated in vacuo to give 4.01 g. of (cis)-1,2-cyclohexanedicarboxylic acid, mono(phenylmethyl)ester as a clear very light yellow oil.

(b) (cis)-N-[N-[(2-Carboxycyclohexyl)carbonyl]-L-phenylalanyl]-L-leucine,bis(phenylmethyl)ester A mixture of (cis)-1,2-cyclohexanedicarboxylic acid, mono(phenylmethyl) ester (1.05 g., 4.0 mmole), L-phenylalanyl-L-leucine, phenylmethyl ester, hydrochloride (1.62 g., 4.0 mmole), 1-hydroxybenzotriazole hydrate (0.54 g., 4.0 mmole), and diisopropylethylamine (0.7 ml., 4.0 mmole) in tetrahydrofuran (50 ml.) is cooled to 0° in an ice/methanol bath with vigorous stirring. A solution of dicyclohexylcarbodiimide (0.82 g., 4.0 mmole) in tetrahydrofuran (8 ml.) is added dropwise, while maintaining the reaction temperature below 5°. The mixture is stirred overnight, warming to room temperature, then filtered and the filtrate concentrated in vacuo. The clear, yellow residue is taken up in ethyl acetate (50 ml.) (gentle warming), washed with 10% potassium bisulfate, 50% brine, saturated sodium bicarbonate, and 50% brine (30 ml. each), dried ($Na_2SO_4$), and concentrated in vacuo to a semi-solid oily material (2.55 g.). This material is applied to a column of silica gel (230–400 mesh, 120 g.) and eluted with 7:2 hexane/acetone. After a void volume of 250 ml., 50 ml. fractions are taken and fractions numbered 14–20 are pooled and concentrated in vacuo to give 1.69 g. of (cis)-N-[N-[(2-carboxycyclohexyl)carbonyl]-L-phenylalanyl]-L-leucine, bis(phenylmethyl)ester as a viscous, clear, colorless oil.

(c) (cis)-N-[N-[(2-Carboxycyclohexyl)carbonyl]-L-phenylalanyl]-L-leucine

To a solution of the bis(phenylmethyl)ester product form part (b) (1.69 g., 2.76 mmole) in 95% ethanol (60 ml.), under argon is added 10% palladium on carbon catalyst (0.15 g.). The mixture is placed under one atmosphere of hydrogen and stirred overnight at room temperature. The catalyst is filtered off and the filtrate is concentrated in vacuo to a white foam (1.25 g.). This material is applied to a column of silica gel (230–400 mesh, 70 g.) and eluted with 5:1 toluene/acetic acid. After a void volume, fractions of 25 ml. are collected. Fractions numbered 9–16 are pooled and concentrated to approximately half volume whereupon a white precipitate begins to form. Ether (100 ml.) and hexane (400 ml.) are added and the mixture is allowed to stand for one hour at room temperature. The gummy white solid which forms is then filtered, washed with hexane (twice), and dried in vacuo to give 0.86 g. of (cis)-N-[N-[(2-carboxycyclohexyl)carbonyl]-L-phenylalanyl]-L-leucine; m.p. 84–122°. TLC (silica gel, $R_f$=0.30, 0.34; 5:1 toluene/acetic acid).

Anal. Calc'd. for $C_{23}N_{32}N_2O_6$: C, 63.87; H, 7.45; N, 6.47. Found: C, 63.70; H, 7.59; N, 6.18.

EXAPMLES 37–82

Following the procedure of Example 22 but substituting for the L-alanyl-L-proline, phenylmethyl ester the imino or amino acid ester shown below in Col. I one obtains the diester product shown in Col. II. Hydrogenation or chemical treatment yields the corresponding diacid which can then be converted to the disalt.

Col. I

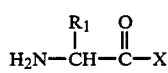

Col. II

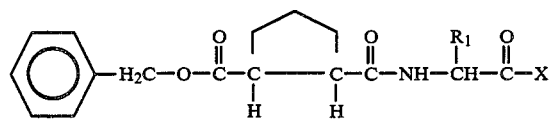

| Example | $R_1$ | X |
|---|---|---|
| 37 | —$CH_3$ | 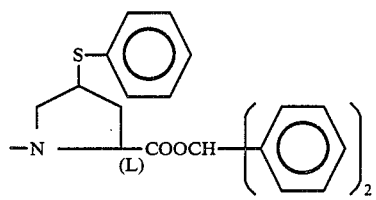 |

-continued

Col. I

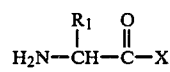

Col. II

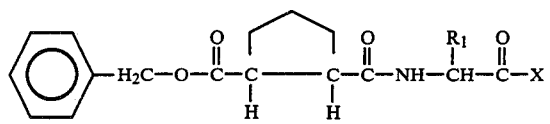

| Example | $R_1$ | X |
|---|---|---|
| 38 | —$CH_3$ | (spiro dithiolane-piperidine with —COOCH(phenyl)$_2$, L) |
| 39 | —$CH_3$ | (spiro dithiane-piperidine with —COOCH(phenyl)$_2$, L) |
| 40 | —$CH_3$ | (spiro dioxolane-piperidine with —COOCH$_2$phenyl, L) |
| 41 | —$CH_3$ | (methyl-substituted spiro dithiolane-piperidine with —COOCH(phenyl)$_2$, L) |
| 42 | —$CH_3$ | (4,4-dichloropiperidine with —COOCH$_2$phenyl, L) |
| 43 | —$CH_3$ | (4-cyclohexylpiperidine with —COOCH$_2$phenyl, L) |

-continued
Col. I
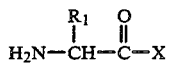
Col. II
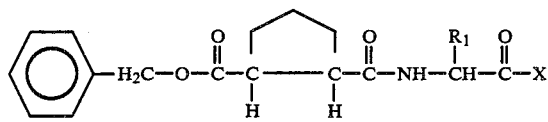
| Example | R₁ | X |
|---|---|---|
| 44 | —CH₃ | 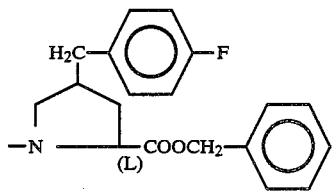 |
| 45 | —CH₃ | 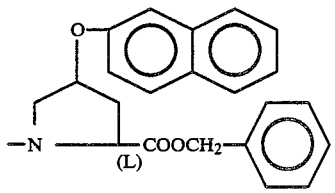 |
| 46 | —CH₃ | 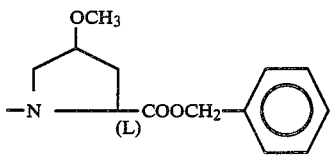 |
| 47 | —CH₃ | 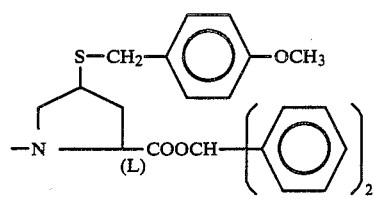 |
| 48 | —CH₃ | 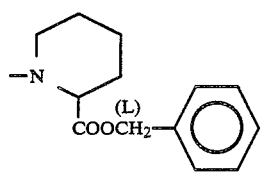 |
| 49 | —CH₃ | 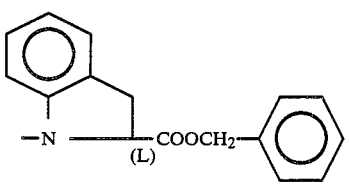 |

-continued
Col. I
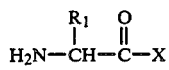
Col. II
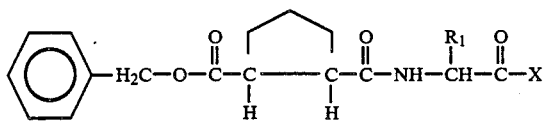
| Example | R₁ | X |
|---|---|---|
| 50 | —CH₃ | —N(2-benzyl-phenyl)(L)-COOCH₂-phenyl |
| 51 | —CH₃ | —NH—CH₂—COOCH₂-phenyl |
| 52 | —CH₃ | —NH—CH(L)(CH₂-phenyl)—COOCH₂-phenyl |
| 53 | —CH₃ | —NH—CH(L)(CH₃)—COOCH₂-phenyl |
| 54 | —CH₃ | —NH—CH(L)(CH₂CH(CH₃)₂)—COOCH₂-phenyl |
| 55 | —CH₃ | —NH—CH(L)(CH₂-(4-OCH₂-phenyl)phenyl)—COOCH₂-phenyl |

-continued
Col. I
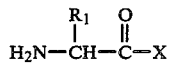
Col. II
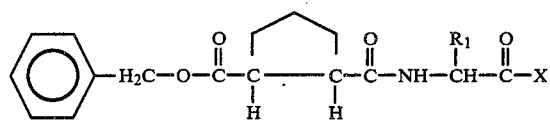
| Example | R₁ | X |
|---|---|---|
| 56 | —CH₃ | 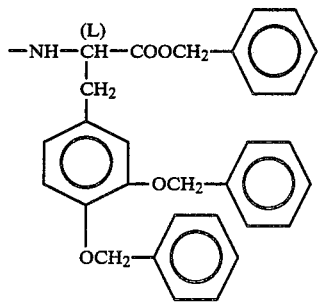 |
| 57 | —CH₃ | 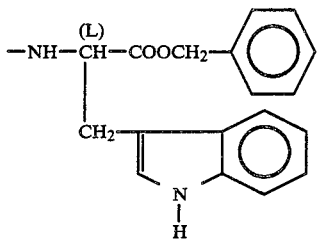 |
| 58 | —CH₃ | 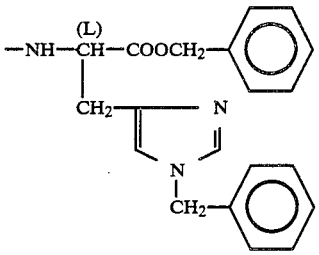 |
| 59 | —CH₃ | 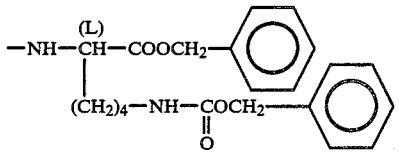 |
| 60 | —CH₃ | 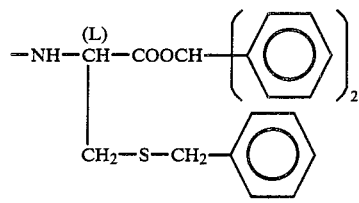 |

-continued
Col. I
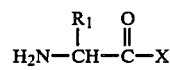
Col. II
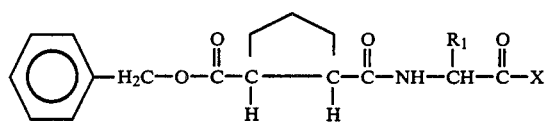
| Example | R₁ | X |
|---|---|---|
| 61 | —CH₃ | 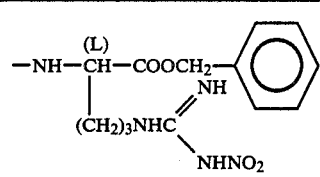 |
| 62 | —CH₃ | 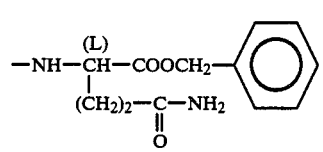 |
| 63 | —CH₃ | 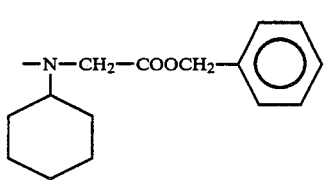 |
| 64 | —CH₃ | 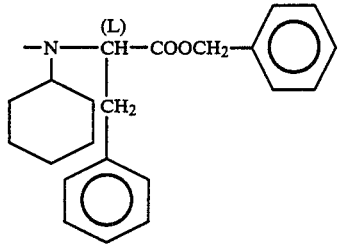 |
| 65 | —CH₃ | 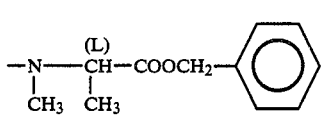 |
| 66 | —CH₃ | 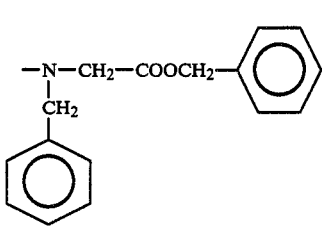 |
| 67 | —H | 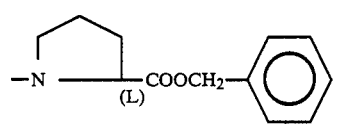 |

-continued
Col. I
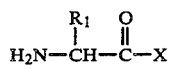
Col. II
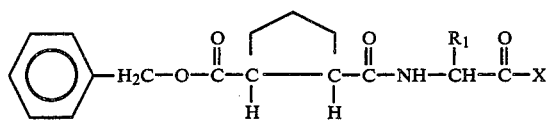
| Example | R₁ | X |
|---|---|---|
| 68 | $-C_2H_5$ | 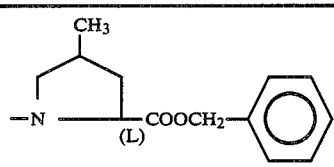 |
| 69 | $-C(CH_3)_3$ | 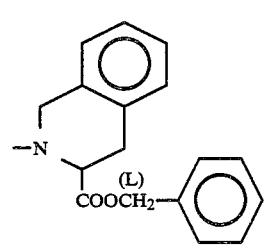 |
| 70 | 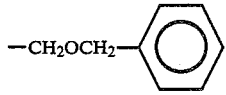 | 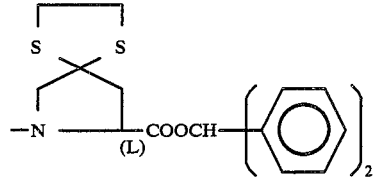 |
| 71 | 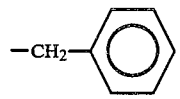 | 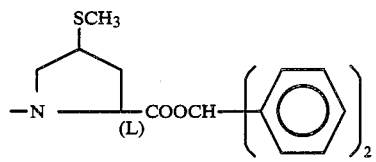 |
| 72 | 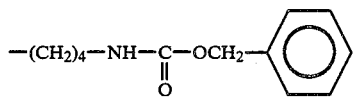 | 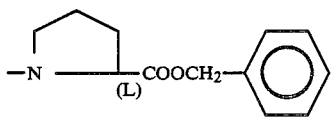 |
| 73 | 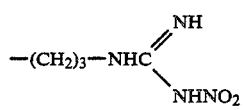 | 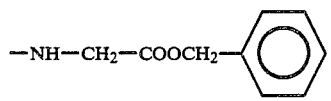 |
| 74 | 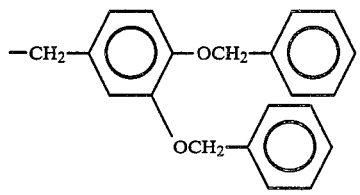 | 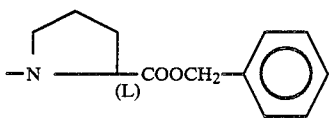 |

-continued
Col. I
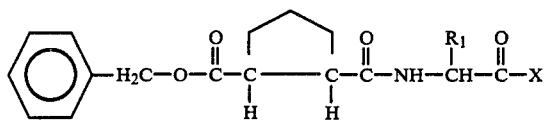
Col. II
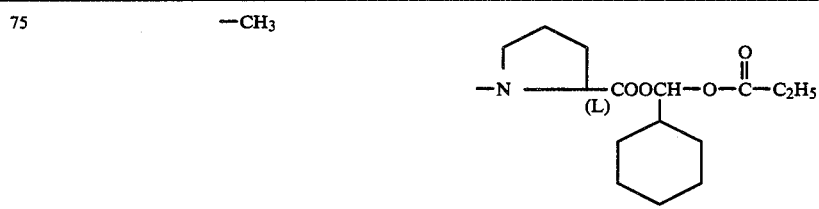
| Example | R₁ | X |
|---|---|---|
| 75 | —CH₃ | 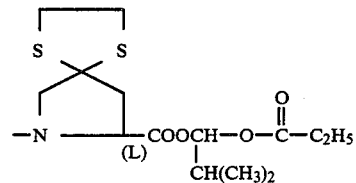 |
| 76 | —CH₃ | 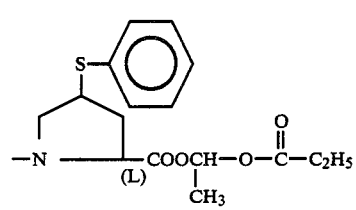 |
| 77 | —CH₃ | 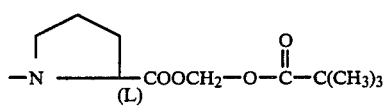 |
| 78 | —CH₃ | 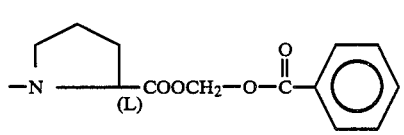 |
| 79 | —CH₃ | 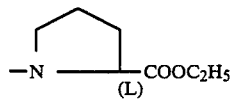 |
| 80 | —CH₃ | 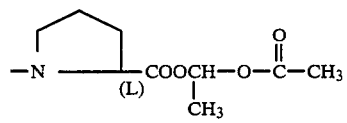 |
| 81 | —CH₃ | |

Col. I

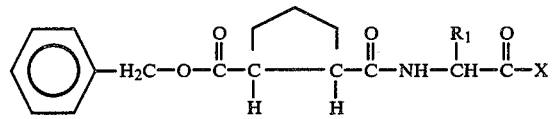

Col. II

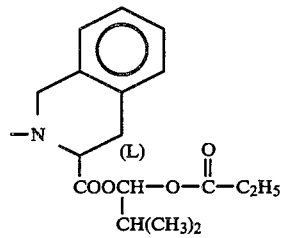

| Example | R₁ | X |
|---|---|---|
| 82 | —CH₃ | (structure shown: tetrahydroisoquinoline-N linked via —COOCH(CH(CH₃)₂)—O—C(O)—C₂H₅, (L)) |

The $R_1$ protecting groups shown in Examples 70 and 72 to 74 and the $R_9$ protecting groups shown in Examples 55, 56, 58 and 59 to 61 are removed as the last step in the synthesis. The $R_6$ ester groups shown in Examples 75 to 82 are not removed.

Similarly, the imino or amino acid esters of Col. I can be employed in the procedures of Examples 1 to 21 and 23 to 32 to obtain other compounds within the scope of this invention.

EXAMPLE 83

(cis)-1-[N-[[2-[[(2,2-Dimethyl-1-oxopropoxy)methoxy]carbonyl]cyclopentyl]carbonyl]-L-alanyl]-L-proline, lithium salt (a) (cis)-Cyclopentane-1,2-dicarboxylic acid, mono[(2,2-dimethyl-1-oxopropoxy)methyl] ester (cis)-Cyclopentane-1,2-dicarboxylic anhydride is reacted with chloromethyl pivalate in the presence of diisopropylethylamine to yield (cis)-cyclopentane-1,2-dicarboxylic acid, mono[(2,2-dimethyl-1-oxopropoxy)methyl] ester.

(b) (cis)-1-[N-[[2-[[(2,2-Dimethyl-1-oxopropoxy)methoxy]carbonyl]cyclopentyl]carbonyl]-L-alanyl]-L-proline, phenylmethyl ester The (cis)-cyclopentane-1,2-dicarboxylic acid, mono[(2,2-dimethyl-1-oxopropoxy)methyl] ester from part (a) is reacted in an equimolar amount with L-alanyl-L-proline, phenylmethyl ester tosylate salt in tetrahydrofuran in the presence of equimolar amounts of dicyclohexylcarbodiimide, 1-hydroxybenzotriazole hydrate, and diisopropylethylamine. The reaction mixture is worked up according to the procedure of Example 22(c) to give (cis)-1-[N-[[2-[[(2,2-dimethyl-1-oxopropoxy)methoxy]carbonyl]cyclopentyl]carbonyl]-L-alanyl]-L-proline, phenylmethyl ester.

(c) (cis)-1-[N-[[2-[[(2,2-Dimethyl-1-oxopropoxy)methoxy]carbonyl]cyclopentyl]carbonyl]-L-alanyl]-L-proline, lithium salt The phenylmethyl ester product from part (b) is hydrogenated and the crude diacid product is treated with lithium hydroxide and worked up according to the procedure of Example 22 (d) to give (cis)-1-[N-[[2-[[(2,2-dimethyl-1-oxopropoxy)methoxy]carbonyl]cyclopentyl]carbonyl]-L-alanyl]-L-proline, lithium salt.

EXAMPLES 84–88

Following the procedure of Example 83 but employing the alkylating agent shown in Col. I in place of the chloromethyl pivalate, one obtains the product listed in Col. II.

| Example | Col. I | Col. II |
|---|---|---|
| 84 | Br—CH₂—O—C(O)—CH₃ | (cis)-1-[N—[[2-[[(acetyloxy)methoxy]carbonyl]cyclopentyl]carbonyl]-L-alanyl]-L-proline, lithium salt |
| 85 | Cl—CH(CH₃)—O—C(O)—C₂H₅ | (cis)-1-[N—[[2-[[1-(ethylcarbonyloxy)ethoxy]carbonyl]cyclopentyl]carbonyl]-L-alanyl]-L-proline, lithium salt |
| 86 | Cl—CH₂—O—C(O)—C₆H₅ | (cis)-1-[N—[[2-[[(benzoyloxy)methoxy]carbonyl]cyclopentyl]carbonyl]-L-alanyl]-L-proline, lithium salt |
| 87 | Cl—CH(CH(CH₃)₂)—O—C(O)—C₂H₅ | (cis)-1-[N—[[2-[[2-methyl-1-(1-oxopropoxy)propoxy]carbonyl]cyclopentyl]carboxyl]-L-alanyl]-L-proline, lithium salt |

| Example | Col. I | Col. II |
|---|---|---|
| 88 | 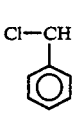 | (cis)-1-[N—[[2-[[cyclohexyl(1-oxopropoxy)methoxy]carbonyl]-cyclopentyl]carboxyl]-L-alanyl]-L-proline, lithium salt |

In a similar manner, esters of the products of Examples 1 to 21 and 23 to 82 can be prepared.

EXAMPLE 89

(trans)-1-[N-[(2-Carboxycyclohexyl)carbonyl]-L-alanyl]-L-proline, disodium salt (trans)-1-[N-[(2-Carboxycyclohexyl)carbonyl]-L-alanyl]-L-proline (1 mmole) is dissolved in water (50 ml.). Aqueous sodium bicarbonate (0.1 N, 20 ml.) is added and the aqueous solution is lyophilized. It is then dissolved in water (10 ml.) and applied on a column of Sephadex chromatography gel G-10 and eluted with water. Fractions containing the desired product are pooled and lyophilized to give (trans)-1-[N-[(2-carboxycyclohexyl)carbonyl]-L-alanyl]-L-proline, disodium salt.

In a similar manner disodium or dipotassium salts of any of Examples 1 to 24 and 26 to 82 and sodium or potassium salts of Examples 83 to 88 can be prepared.

EXAMPLE 90

1000 tablets each containing the following ingredients:

| | |
|---|---|
| (trans)-1-[N—[(2-Carboxy-cyclohexyl)carbonyl]-L-alanyl]-L-proline, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. | are prepared from sufficient bulk quantities by mixing the (trans)-1-[N-[(2-carboxycyclohexyl)carbonyl]-L-alanyl]-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 88 can be prepared.

A similar procedure can be employed to form tablets containing 50 mg. of active ingredient.

EXAMPLE 91

Two piece #1 gelatin capsules each containing 50 mg. of (cis)-1-[N-[(2-carboxycyclopentyl)carbonyl]-L-alanyl]-L-proline, disodium salt are filled with a mixture of the following ingredients:

| | |
|---|---|
| (cis)-1-[N—[(2-Carboxycyclopentyl)carbonyl]-L-alanyl]-L-proline, disodium salt | 50 mg. |
| Magnesium stearate | 7 mg. |
| Lactose | 193 mg. |
| | 250 mg. |

In a similar manner capsules containing 50 mg. of the product of any of Examples 1 to 21 and 23 to 89 can be prepared.

EXAMPLE 92

An injectable solution is prepared as follows:

| | |
|---|---|
| (S)—2-[2-[[[(trans)-2-Carboxycyclohexyl]carbonyl]-amino]-1-oxopropyl]-1,2,3,4-tetrahydro-3-isoquinolinecarboxylic acid, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 32 and 34 to 89.

EXAMPLE 93

1000 tablets each containing the following ingredients:

| | |
|---|---|
| (l-trans)-1-[N—[(2-Carboxycyclohexyl)carbonyl]-L-alanyl]-L-proline, disodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficent bulk quantities by slugging the (l-trans)-1-[N-[(2-carboxycyclohexyl)carbonyl]-L-alanyl]-L-proline, disodium salt, Avicel and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 26 and 28 to 89.

What is claimed is:

1. A compound of the formula $$R-\underset{H}{\overset{O}{\overset{\|}{C}}}-\overset{Z}{\overset{\frown}{C}}-\underset{H}{C}-\overset{O}{\overset{\|}{C}}-NH-\underset{R_1}{CH}-\overset{O}{\overset{\|}{C}}-\underset{R_8}{N}-\underset{R_9}{CH}-COOR_6$$

and a pharmaceutically acceptable salt thereof wherein:

R is hydroxy, lower alkoxy, lower alkyl,

[structure: R_14-phenyl-(CH_2)_n—], R_{18}—C(=O)—O—HC(R_{17})—O—,

[structure: R_14-phenyl-O—], amino, HO—NH—, lower alkoxy-HN—, or MO—;

$R_1$ is hydrogen, lower alkyl, halo substituted lower alkyl,

—(CH_2)_r—phenyl, —(CH_2)_r—phenyl—OH,

—(CH_2)_r—phenyl(OH)(OH), —(CH_2)_r—indolyl,

—(CH_2)_r—imidazolyl, —(CH_2)_r—SH, —(CH_2)_r—OH,

—(CH_2)_r—NH_2, —(CH_2)_r—S—lower alkyl,

—(CH_2)_r—NH—C(=NH)(NH_2), or —(CH_2)_r—C(=O)—NH_2;

$R_8$ is hydrogen, lower alkyl, cycloalkyl of 3 to 7 carbons, or

—(CH_2)_n—phenyl;

$R_9$ is hydrogen, lower alkyl,

—(CH_2)_r—phenyl, —(CH_2)_r—phenyl—OH,

—(CH_2)_r—OH, —(CH_2)_r—phenyl(OH)(OH),

—(CH_2)_r—indolyl, —(CH_2)_r—imidazolyl,

—(CH_2)_r—NH_2, —(CH_2)_r—SH, —(CH_2)_r—S—lower alkyl,

—(CH_2)_r—NH—C(=NH)(NH_2), or —(CH_2)_r—C(=O)—NH_2;

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

n is zero one, two, three, or four;

r is an integer from 1 to 4;

$R_6$ is hydrogen, lower alkyl, benzyl, benzhydryl, salt forming ion, or

—CH(R_{17})—O—C(=O)—R_{18};

$R_{17}$ is hydrogen, lower alkyl, cycloalkyl, or phenyl;

$R_{18}$ is hydrogen, lower alkyl, lower alkoxy or phenyl;

M is a salt forming ion; and

Z completes a cycloalkyl ring of 3 to 10 carbons, said cycloalkyl ring in which one of the carbon atoms is substituted by a lower alkyl of 1 to 4 carbons, lower alkoxy of 1 to 4 carbons, lower alkylthio of 1 to 4 carbons, halo, trifluoromethyl, or hydroxy group, a cycloalkenyl ring of 5 to 7 carbons, or a cycloalkadienyl ring of 6 or 7 carbons.

2. A compound of claim 1 wherein:

$R_1$ and $R_9$ are independently selected from the group consisting of hydrogen, straight or branched chain lower alkyl of 1 to 4 carbons, —CH_2OH, —CH_2—phenyl, —CH_2—phenyl—OH, —CH_2—phenyl(OH)(OH), —CH_2—indolyl, —CH_2—imidazolyl, —(CH_2)_4—NH_2, —CH_2—SH, -continued

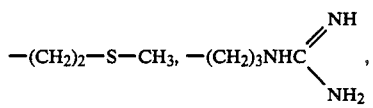

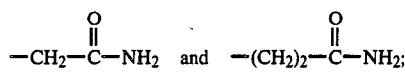

R_6 is hydrogen, an alkali metal salt ion, straight or branched chain alkyl of 1 to 4 carbons or

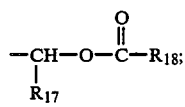

R_17 is hydrogen, straight or branched chain lower alkyl of 1 to 4 carbons, or cyclohexyl;
R_18 is straight or branched chain lower alkyl of 1 to 4 carbons or phenyl; and
R_8 is hydrogen or cycloalkyl of 5 to 7 carbons.

3. A compound of claim 2 wherein:

Z completes a cycloalkyl ring of 4 to 7 carbons, a cycloalkyl ring of 4 to 7 carbons wherein one of the carbons is substituted by a methyl, methoxy, methylthio, Cl, Br, F, or hydroxy, or a cyclohexenyl ring;

R is hydroxy, ethoxy, —OM, or

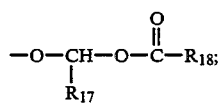

and

M is an alkali metal salt ion.

4. A compound of claim 3 having the formula

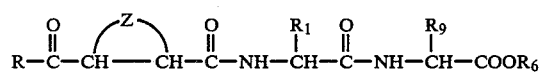

wherein
R_6 is hydrogen, ethyl,

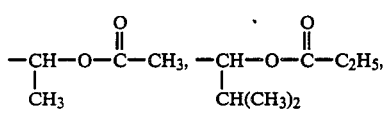

-continued

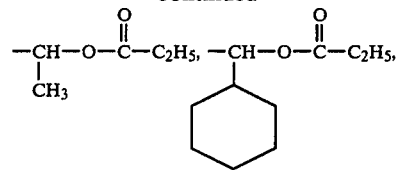

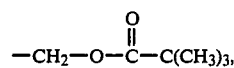

or an alkali metal salt ion; and
R is hydroxy or —OM wherein M is an alkali metal salt ion.

5. A compound of claim 4 wherein
R_1 is

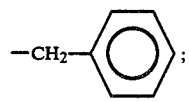

R_9 is —CH_2CH(CH_3)_2;
Z completes a cyclohexyl ring;
R is hydroxy or —OM;
R_6 is hydrogen or —M; and
M is an alkali metal salt ion.

6. The compound of claim 5, (trans)-N-[N-[(2-carboxycyclohexyl)carbonyl]-L-phenylalanyl]-L-leucine.

7. The compound of claim 5, (cis)-N-[N-[(2-carboxycyclohexyl)carbonyl]-L-phenylalanyl]-L-leucine.

8. The method of treating hypertension in a mammlian specie which comprises administering an effective amount of a composition comprising a pharmaceutically acceptable carrier and hypotensively active compound of the formula

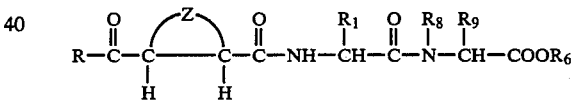

wherein R, R_1, R_6, R_8, R_9, and Z are as defined in claim 1.

9. The method of alleviating pain in a mammalian specie which comprises administering an effective amount of a composition comprising a pharmaceutically acceptable carrier and an enkephalianase inhibitor of formula

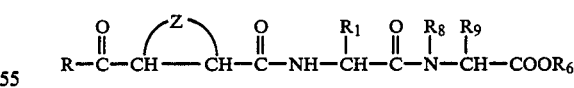

wherein R, R_1, R_6, R_8, R_9, and Z are as defined in claim 1.

* * * * *